US012773211B2

(12) United States Patent
Seddon

(10) Patent No.: US 12,773,211 B2
(45) Date of Patent: Oct. 27, 2026

(54) MAGNETIC COMPRESSION ANASTOMOSIS DEVICE WITH MULTIPIECE VERTEBRA

(71) Applicant: G.I. Windows, Inc., Westwood, MA (US)

(72) Inventor: Dane T. Seddon, Boston, MA (US)

(73) Assignee: G.I. Windows, Inc., Canton, MA (US)

( * ) Notice: Subject to any disclaimer, the term of this patent is extended or adjusted under 35 U.S.C. 154(b) by 83 days.

(21) Appl. No.: 19/029,652

(22) Filed: Jan. 17, 2025

(65) Prior Publication Data

US 2025/0160836 A1 May 22, 2025

Related U.S. Application Data

(63) Continuation-in-part of application No. 18/230,066, filed on Aug. 3, 2023, now Pat. No. 12,201,300.

(60) Provisional application No. 63/395,570, filed on Aug. 5, 2022.

(51) Int. Cl.

| | |
|---|---|
| ***A61B 17/32*** | (2006.01) |
| ***A61B 17/11*** | (2006.01) |
| ***A61B 17/12*** | (2006.01) |
| ***A61B 34/00*** | (2016.01) |
| *A61B 17/00* | (2006.01) |

(52) U.S. Cl.

CPC ........ *A61B 17/11* (2013.01); *A61B 17/12013* (2013.01); *A61B 17/320016* (2013.01); *A61B 34/73* (2016.02); *A61B 2017/00862* (2013.01); *A61B 2017/00867* (2013.01); *A61B 2017/00876* (2013.01)

(58) Field of Classification Search

CPC ..... A61B 17/1114; A61B 17/32; A61B 17/11; A61B 2017/00867; A61B 2017/00876; A61B 2017/1132; A61B 2017/1117; A61B 2017/1139

See application file for complete search history.

(56) References Cited

U.S. PATENT DOCUMENTS

| | | | | |
|---|---|---|---|---|
| 4,197,840 A * | 4/1980 | Beck | ..................... | H01F 7/0221 600/12 |
| 2016/0262761 A1 * | 9/2016 | Beisel | ................. | A61B 17/1114 |

* cited by examiner

*Primary Examiner* — Anh T Dang

(74) *Attorney, Agent, or Firm* — Nutter McClennen & Fish LLP

(57) ABSTRACT

A magnetic compression anastomosis device comprises a plurality of interconnected vertebrae including a first vertebra and a second vertebra, wherein each of the first vertebra and the second vertebra is a multipiece vertebra comprising a magnet at least partially encapsulated by a vertebra skin, and wherein the first vertebra and the second vertebra are interconnected by a cylindrical roller and at least one flex element, the roller and the at least one flex element at least partially encapsulated by the first vertebra skin and the second vertebra skin, the roller configured to allow the first and second vertebra to pivot through a predetermined range of rotation in a device plane between at least a delivery configuration and an assembled configuration while constraining movement in other degrees of freedom, the at least one flex element biasing the first and second vertebra toward the assembled configuration.

20 Claims, 28 Drawing Sheets

(d)

(c)

(b)

(a)

MAGNETIC COMPRESSION ANASTOMOSIS DEVICE WITH MULTIPIECE VERTEBRA

CROSS-REFERENCE TO RELATED APPLICATION(S)

This patent application is a continuation-in-part (CIP) of U.S. patent application Ser. No. 18/230,066 entitled MAGNETIC COMPRESSION ANASTOMOSIS DEVICE WITH MULTIPIECE VERTEBRA filed Aug. 3, 2023, which claims the benefit of U.S. Provisional Patent Application No. 63/395,570 entitled SUPPORT FOR MAGNETIC SEGMENTS OF A MAGNETIC ANASTOMOSIS DEVICE filed Aug. 5, 2022, each of which is hereby incorporated herein by reference in its entirety.

FIELD OF INVENTION

The invention relates to deployable magnetic compression devices, and, more particularly, to systems, devices, and methods for the delivery, deployment, and positioning of magnetic compression devices at a desired site so as to improve the accuracy of anastomoses creation between tissues, organs, or the like.

BACKGROUND

Bypasses of the gastroenterological (GI), cardiovascular, or urological systems are typically formed by cutting holes in tissues at two locations and joining the holes with sutures or staples. A bypass is typically placed to route fluids (e.g., blood, nutrients) between healthier portions of the system, while bypassing diseases or malfunctioning tissues. The procedure is typically invasive, and subjects a patient to risks such as bleeding, infection, pain, and adverse reaction to anesthesia. Additionally, a bypass created with sutures or staples can be complicated by post-operative leaks and adhesions. Leaks may result in infection or sepsis, while adhesions can result in complications such as bowel strangulation and obstruction. While traditional bypass procedures can be completed with an endoscope, laparoscope, or robot, it can be time consuming to join the holes cut into the tissues. Furthermore, such procedures require specialized expertise and equipment that is not available at many surgical facilities.

As an alternative to sutures or staples, surgeons can use mechanical couplings or magnets to create a compressive anastomosis between tissues. For example, compressive couplings or paired magnets can be delivered to tissues to be joined. Because of the strong compression, the tissue trapped between the couplings or magnets is cut off from its blood supply. Under these conditions, the tissue becomes necrotic and degenerates, and at the same time, new tissue grows around points of compression, e.g., on the edges of the coupling. With time, the coupling can be removed, leaving a healed anastomosis between the tissues.

Nonetheless, the difficulty of placing the magnets or couplings limits the locations that compressive anastomosis can be used. In most cases, the magnets or couplings have to be delivered as two separate assemblies, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency. Furthermore, placement of the magnets or couplings can be imprecise, which can lead to anastomosis formation in locations that is undesirable or inaccurate.

Thus, there still remains a clinical need for reliable devices and minimally-invasive procedures that facilitate compression anastomosis formation between tissues in the human body.

SUMMARY

During the deployment of a self-forming magnetic array, control of the individual magnetic pieces is critical. Limiting the degrees of freedom to a specific set of parameters provides durability as well as improved geometric shape control. When connecting two separate magnets it is also important that the geometric shapes align to produce a compression region with high enough pressure to shut down fluidic exchange to the tissue in the inner periphery of the geometric shape created by the self-forming array.

An embodiment of the present invention utilizes independent magnets connected by a multipiece vertebrae design. Prior innovations utilize a single formed piece of alloy to create the support. The present invention utilizes individual flex segments which connect to flexing armatures, a vertebrae casing, and either a "roller" or an integrated "rolling node" to limit degrees of freedom during formation and increase durability.

During coupling of two magnetic arrays, the ability to sense the mating array is more easily done with a single magnetic pole face. An embodiment of the invention provides for an internal skeleton that forces the same pole faces together.

More particularly, in accordance with one embodiment of the invention, a magnetic compression anastomosis device comprises a plurality of interconnected vertebrae including a first vertebra and a second vertebra, wherein each of the first vertebra and the second vertebra is a multipiece vertebra comprising a magnet at least partially encapsulated by a vertebra skin, and wherein the first vertebra and the second vertebra are interconnected by a cylindrical roller and at least one flex element, the roller and the at least one flex element at least partially encapsulated by the first vertebra skin and the second vertebra skin, the roller configured to allow the first and second vertebra to pivot through a predetermined range of rotation in a device plane between at least a delivery configuration and an assembled configuration while constraining movement in other degrees of freedom, the at least one flex element biasing the first and second vertebra toward the assembled configuration.

In various alternative embodiments, the vertebra skin may include at least one of a metal alloy, a polymer, or a composite material, e.g., a shape memory material. The vertebra skin may be configured with various types of features such as at least one tissue cutting element, at least one tissue compression element, and/or tissue securing element. Each vertebra skin may include male nodes and female nodes at opposing ends of the vertebra skin, in which case the male nodes may be configured to secure the roller in place. The roller may be, for example, a hollow cylinder or a solid cylinder. The flex element may include a flexible bar (e.g., including a spring mechanism such as a shape memory material) or a pair of U-brackets operationally coupled to the roller. In some embodiments, the roller and the flex element may be implemented using a coil or torsion spring. The vertebrae may be aligned in a substantially linear arrangement in the delivery configuration and/or may be arranged in a circular or polygon arrangement in the assembled configuration. The vertebrae may include a proximal end vertebra and a distal end vertebra that magnetically couple to one another in the assembled configuration.

In accordance with another embodiment of the invention, a magnetic compression anastomosis system comprises a delivery device comprising a lumen and at least one magnetic compression anastomosis device as described above, predisposed within the lumen of the delivery device in the delivery configuration.

Additional embodiments may be disclosed and claimed.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

Figure 1:
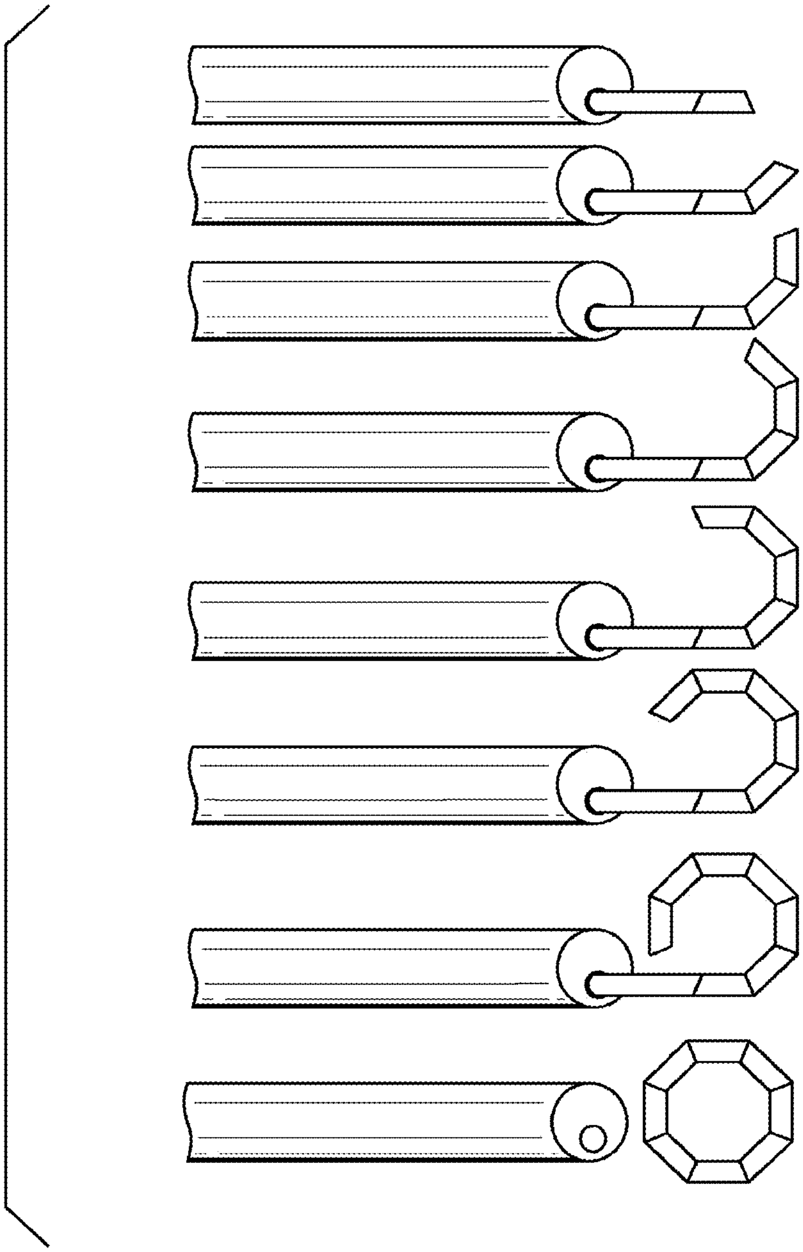
FIG. 1 shows a magnet assembly delivered through an endoscope instrument channel such that the individual magnets self-assemble into a larger magnetic structure—in this particular case, an octagon.

It should be noted that the foregoing figures and the elements depicted therein are not necessarily drawn to consistent scale or to any scale. Unless the context otherwise suggests, like elements are indicated by like numerals. The drawings are primarily for illustrative purposes and are not intended to limit the scope of the inventive subject matter described herein.

DESCRIPTION OF ILLUSTRATIVE EMBODIMENTS

Exemplary embodiments provide improved devices and techniques for minimally invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

The system generally includes an access device configured to be provided within a hollow body of a patient and assist in the formation of an anastomosis at a target site (a desired anatomical location) within the hollow body for formation of an anastomosis between a first portion of tissue of the hollow body at the target site and a second portion of tissue of an adjacent hollow body, e.g., between the gallbladder and the stomach, between the stomach and the duodenum, between the ileum and the colon, etc. The access device is configured to provide access to the first portion of tissue of the hollow body and further deliver and position a first implantable magnetic anastomosis device. A second implantable magnetic anastomosis device is delivered to the adjacent hollow body, e.g., using the same access device or a second access device. The first and second implantable magnetic anastomosis devices are configured to be magnetically attracted to one another through a defined tissue area of the combined thickness of a wall of the tissues at the target site and exert compressive forces on the defined area to form the anastomosis.

The systems, devices, and methods described herein include, but are not limited to, various access devices for accessing a hollow body of the patient, such as a gall bladder, and securing positioning of the access device for the subsequent placement of one of a pair of magnetic anastomosis compression devices. The systems, devices, and methods described herein further include various delivery devices for delivering at least one of the pair of magnetic anastomosis compression devices to the target site, wherein, in some instances, a delivery device consistent with the present disclosure may assist in the deployment of at least one of the pair of magnetic anastomosis compression devices and subsequent securing to the target site and/or coupling the pair of magnetic anastomosis compression devices to one another. The systems, devices, and methods described herein include various embodiments of magnetic anastomosis compression devices and various designs for transitioning from a compact delivery configuration to a larger deployed configuration, generally by way of self-assembling design.

More specifically, exemplary embodiments provide a system including a delivery device for introducing and delivering, via a minimally invasive technique, a pair of magnetic assemblies between adjacent organs to bridge walls of tissue of each organ together to thereby form a passage therebetween (i.e., an anastomosis). The delivery device is particularly useful in delivering the pair of magnetic assemblies to a target site within the gastrointestinal tract to thereby form anastomosis between gastric and gall bladder walls to provide adequate drainage from the gallbladder when blockage is occurring (due to disease or other health-related issues). Accordingly, exemplary embodiments provide improved devices and techniques for minimally invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers, such as stomach or colon cancer.

In an endoscopic procedure, for example, the self-assembling magnetic devices can be delivered using a single endoscope. Exemplary magnetic anastomosis devices may be delivered through an endoscope such that individual magnet segments self-assemble into a larger magnetic structure. When used with the techniques described herein, the devices allow for the delivery of a larger magnetic structures than would otherwise be possible via a small delivery conduit, such as in a standard endoscope, if the devices were deployed as a completed assembly. Larger magnet structures, in turn, allow for the creation of larger anastomoses that are more robust, and achieve greater surgical success. For example, in some cases, resulting anastomosis may have a 1:1 aspect ratio relative to the final dimensions of the assembled magnetic devices. However, exemplary embodiments allow for larger aspect ratios (i.e., a larger anastomosis to form relative to the dimensions of the magnetic assemblies). In particular, prior art systems and methods that include the use of magnets for creating anastomosis are generally limited based on the dimensions of the working channel of the scope or catheter used for delivering such magnets, which, in turn, limits the resulting size of the anastomosis. However, the magnetic assembly design of exemplary embodiments overcome such limitations. For example, the design of the magnetic assembly, notably the coupling of multiple magnetic segments to one another via a support, allow for any number of segments to be included in a single assembly, and thus the resulting anastomosis has a greater size relative to the dimensions of the working channel of the scope. For example, in some embodiments, the resulting anastomosis may include an aspect ratio in the range of 2:1 to 10:1 or greater.

The magnetic anastomosis devices generally comprise magnetic segments that can assume a delivery conformation and a deployed configuration. The delivery configuration is typically linear so that the device can be delivered to a tissue via a laparoscopic "keyhole" incision or with delivery via a natural pathway, e.g., via the esophagus, with an endoscope or similar device. Additionally, the delivery conformation is typically somewhat flexible so that the device can be guided through various curves in the body. Once the device is delivered, the device will assume a deployed configuration of the desired shape and size by converting from the delivery configuration to the deployed configuration automatically. The self-conversion from the delivery configuration to the deployment configuration is directed by coupling structures that cause the magnetic segments to move in the desired way without intervention. Exemplary self-assembling magnetic anastomosis devices, such as self-closing, self-opening, and the like, are described in U.S. Pat. Nos. 8,870,898, 8,870,899, 9,763,664, and 10,182,821, the contents of each of which are incorporated by reference herein in their entirety.

During the deployment of a self-forming magnetic array, control of the individual magnetic pieces is critical. Limiting the degrees of freedom to a specific set of parameters provides durability as well as improved geometric shape control. When connecting two separate magnets, it is also important that the geometric shapes align to produce a compression region with high enough pressure to shut down fluidic exchange to the tissue in the inner periphery of the geometric shape created by the self-forming array.

Figure 22:
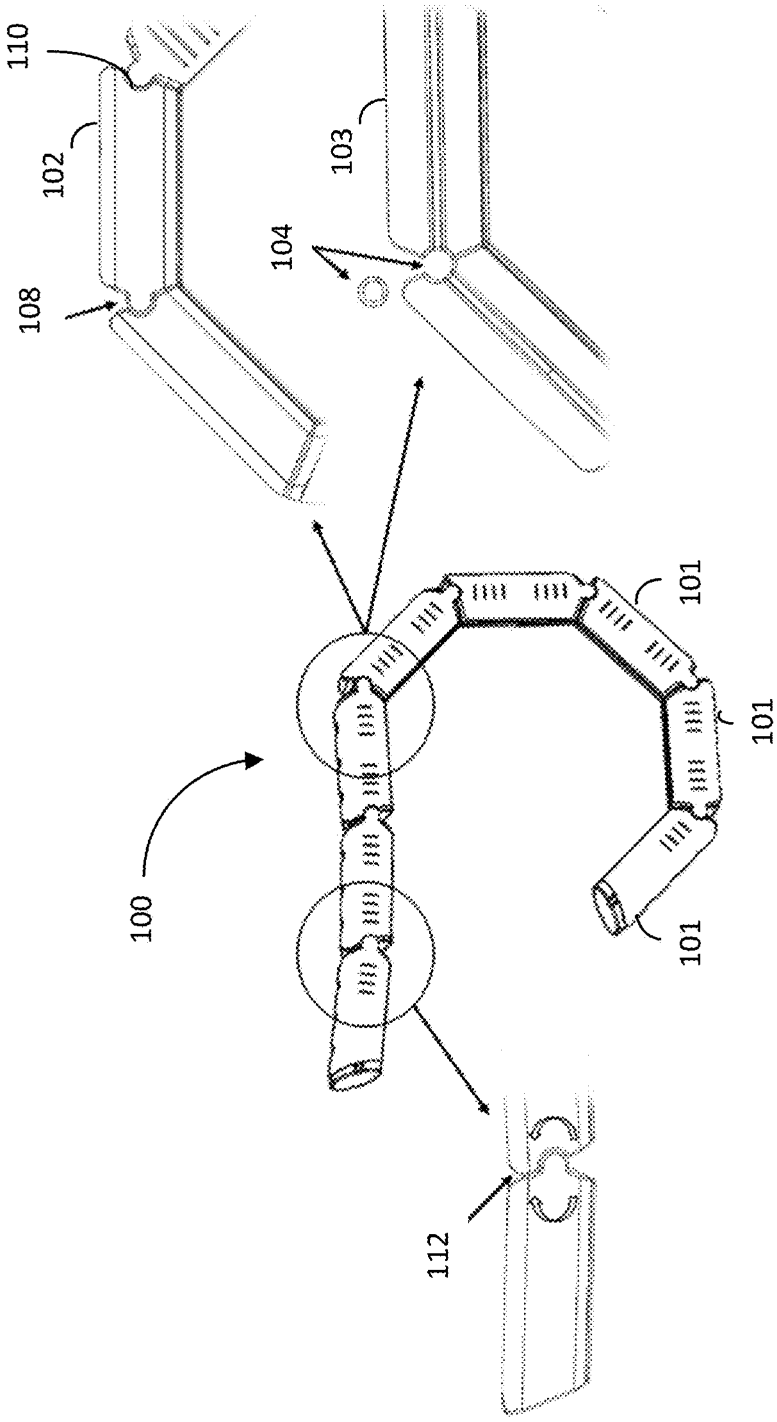
FIG. 22 depicts an exploded view of multipiece vertebrae of a self-assembling magnetic compression anastomosis device in accordance certain embodiments.

In certain embodiments as depicted schematically in FIG. 22, a magnetic compression anastomosis device 100 includes multiple magnetic segments 101 (three magnetic segments 101 out of eight magnetic segments 101 of this embodiment are labeled, although it should be noted that embodiments are not limited to any particular number of magnetic segments). For convenience, the magnetic segments 101 may be referred to herein as vertebrae 101, and each individual magnetic segment 101 may be referred to as a vertebra 101.

The vertebrae 101 are configured to allow for movement between a delivery configuration of the device 100 (which is typically with the vertebrae 101 aligned substantially linearly to fit within a delivery device such as a catheter, endoscope, laparoscope, trocar, needle, or other delivery device) and a fully assembled configuration of the device 100 (e.g., a circular or polygon configuration) while restricting unwanted degrees of freedom such as twisting, over-rotation, under-rotation, and out-of-plane deflection of one or more vertebra that could cause incomplete assembly or non-assembly of the device 100. Thus, embodiments of the device 100 can be self-assembling devices (e.g., automatically and autonomously transitioning into the fully assembled configuration upon delivery) although embodiments additionally or alternatively can include additional elements to assist with or manually place the device 100 into the fully assembled form (e.g., sutures, wires, etc.). For purposes of this discussion, the plane of the device 100 can be considered the plane running through the centers of the vertebrae when in the fully assembled configuration. The vertebrae 101 include a proximal end vertebra and a distal end vertebra that magnetically couple to one another in the assembled configuration such as to form a circular or polygon arrangement.

As discussed in greater detail below, in certain embodiments, each vertebra 101 may be a multipiece vertebra including a vertebra skin 102 that fully or partially encapsulates one or more magnets 103 and other components discussed herein. The device 100 can be configured with different magnetic polarity configurations, e.g., all vertebrae 101 having the same magnetic polarity, vertebrae 101 with alternating magnetic polarities, vertebrae 101 with alternating pairs of magnetic polarities, vertebrae 101, etc. The present invention is not limited to any particular magnetic polarity configurations.

Each pair of adjacent interconnected vertebra 101 is rotatably connected by a cylindrical roller 104. For purposes of this discussion, a cylindrical roller is generally a hollow cylinder (e.g., tubular) although in some embodiments can be a solid cylinder (e.g., a pin) or other element facilitating rotation (e.g., a torsion spring). The roller 104 may be used to provide radial constraint and limit the degrees of freedom thus strengthening the assembly from a torsional standpoint. The roller 104 may be composed of a metal alloy, polymer, and/or composite. The roller 104 is preferably configured to allow rotation of the vertebrae 101 in the device plane, but otherwise to limit other degrees of freedom. The roller 104 may include features such as protrusions or recesses to help secure the roller 104 in between the two vertebra 101 and/or to control the amount of rotation that can occur between the two vertebra 101, e.g., to provide radial constraint and limit the degrees of freedom thus strengthening the assembly from a torsional standpoint. The roller 104 may be composed of any appropriate material such as a metal alloy, polymer, and/or composite. The roller 104 may be a separate component, adapted to fit between two or more magnets 103. Each magnet 103 may include a notch on each end adapted to fit a roller allowing for motion in one plane while restricting motion in other planes.

Figure 23:
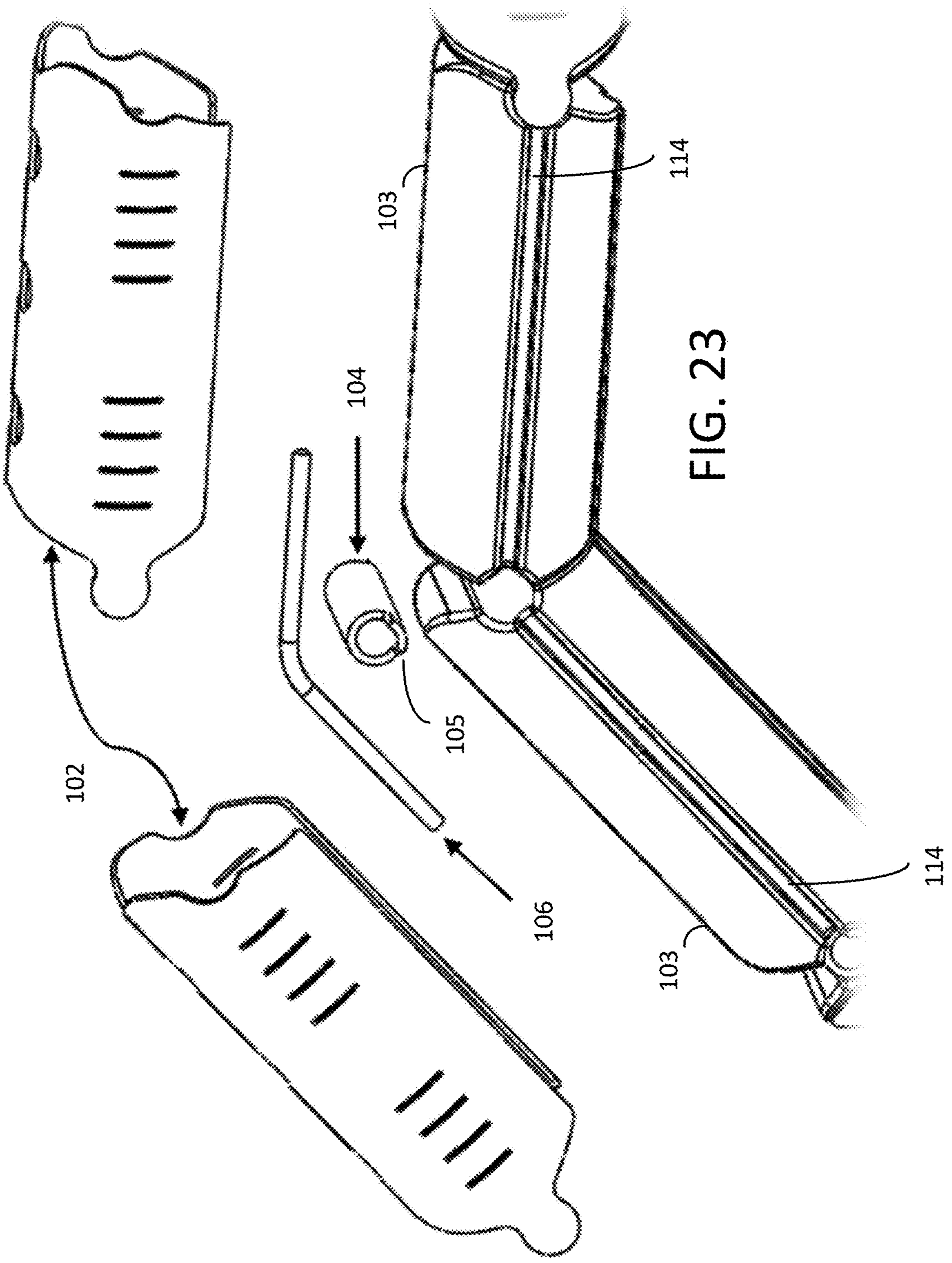
FIG. 23 is an enlarged view of the various components shown in FIG. 22 and also showing an example of a flex element in accordance with certain embodiments.

Each pair of adjacent interconnected vertebra 101 typically also includes a flex element 106 (an example of which is shown in FIG. 23) that helps to move the vertebrae 101 from the delivery configuration to the assembled configuration. For example, the flex element 106 may operate as a spring (e.g., the flex element may include a spring or may be formed from a shape memory material) and may impose a bias toward the assembled configuration so that the vertebrae 101 are biased toward the assembled configuration upon delivery of the device 100. The flex element 106 may be composed of any appropriate material, e.g., a metal alloy, polymer, and/or composite and in particular a shape memory material. In various embodiments, the flex segment is positioned between two vertebrae skins on the outside perimeter of the array. It should be noted, however, that the flex segment may also be positioned on the internal perimeter of the array. The flex segment serves to strengthen the array as well as limit degrees of freedom. The flex member may also serve to aid the array to deploy into the proper assembled geometry.

The vertebra skin 102 may be formed of an appropriate material such as metal alloy, polymer, and/or composite and in particular may be formed of or include a shape memory material. The vertebra skin 102 encapsulates the magnet(s) 103 and helps to secure the roller 104 and flex element 106 within the device 100, forming a protective layer while also restricting degrees of freedom. The vertebra skin 102 may be secured onto the magnet(s) 103 with or without additional fasteners such as screws, pins, adhesive, interlocking elements, etc. Thus, for example, with a magnet 103, a roller 104, and a flex element 106 positioned for assembly, a vertebra skin 102 can be installed over the magnet 103, the roller 104, and the flex element 106 such as to encapsulate the components. As shown, the vertebra skin 102 may incorporate male nodes 108 and female nodes 110 on opposing ends of the vertebra capable of interacting with the opposing gender node on another vertebra. The male node 108 of one segment meshes or joins with the female node 110 of another segment. The incorporated nodes support the movement in one plane while restricting other degrees of freedom. The male nodes 108 may assist with securing the roller 104 and/or the flex element 106 within the device 100. The incorporated nodes may include stops to limit additional degrees of freedom, e.g., to prevent "backwards bending" or excess "forward bending" of the array, as represented in view 112. Stops can provide interference of the vertebrae while allowing a prescribed amount of rotation around the axis of the male and female node interaction.

FIG. 23 is an enlarged view of the various components shown in FIG. 22 and also shows an example of a flex element 106, which, in this example, is in the form of a bar having a central spring section, e.g., formed of a shape memory material. Without limitation, the flex element 106 can be configured to fit within channels 114 of the magnets 103 or in any other configuration (e.g., over or under the roller 104, which may include a flex element support 105 on which the flex element 106 rests to provide a fulcrum for the flex element 106) allowing the flex element 106 to control the movement of the vertebrae 101 such as biasing the vertebrae 101 toward the assembled configuration. Embodiments can include one, two, or more flex elements 106 and related elements such as elements 105 and 114, e.g., a flex element 106 placed on both sides of the vertebrae 101. A flex element 106 may be a unitary device or may include multiple components.

Figure 24:
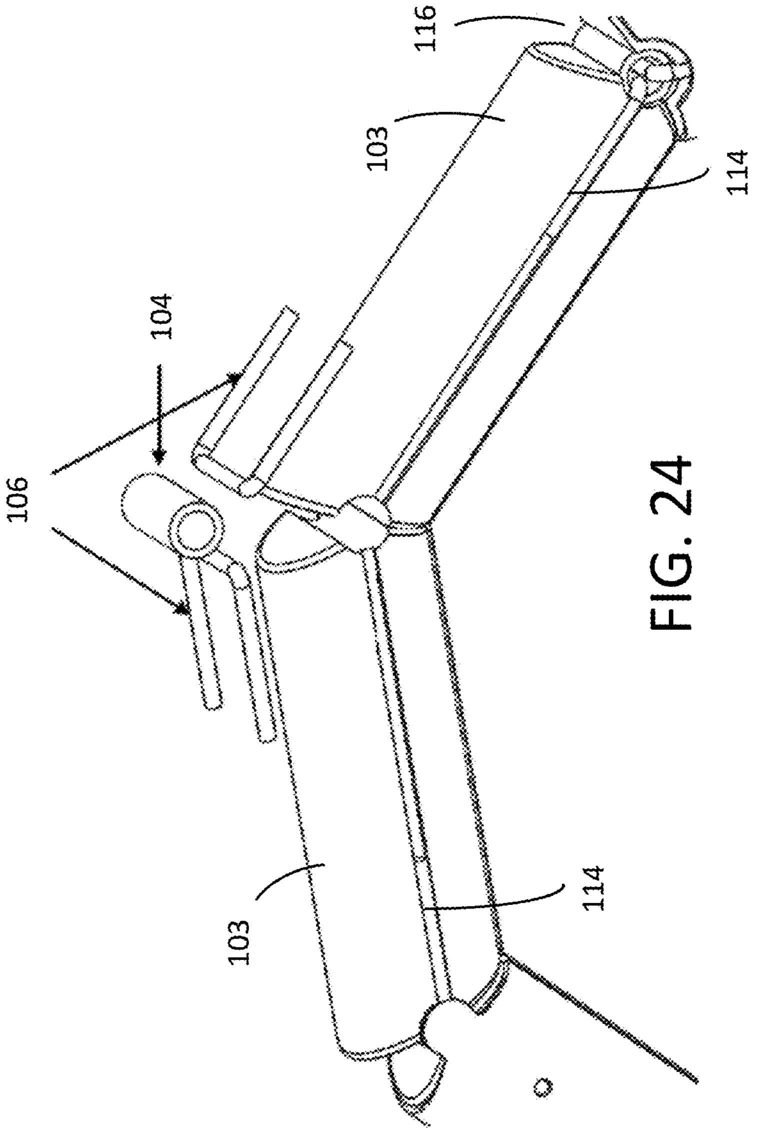
FIG. 24 shows an alternative example of a flex element in accordance with certain embodiments.

FIG. 24 shows an alternative example of a flex element 106, which, in this example, includes two oppositely-oriented U-brackets that, together with the roller 104 and magnets 103 as depicted in view 116, operate as biased springs in a manner similar to the flex element 106 shown and described above with reference to FIG. 23. Specifically, a U-bracket may be placed on each end of a magnetic segment. The U-brackets hold the roller 104 in place while allowing for rotation in one plane but restricting out-of-plane motion. The U-brackets may be composed of any appropriate material, e.g., a metal alloy, polymer, and/or composite and in particular may be formed of or include a shape memory material. The U-brackets allow for movement in a plane while restricting torsional motion and motion in other planes. The roller and U-brackets may fit directly on the magnetic segments, and within the vertebrae skins, e.g., the U-brackets may fit through and be secured by the roller 104, as depicted in view 116, and extend along the length of the magnetic segment, e.g., in channels 114. The roller 104 may include flex element supports such as to secure the U-brackets in a position that allows bias toward the assembled configuration. By interlocking the roller 104 with the magnets 103, the roller 104 and U-brackets 106 serve to provide structure and shape to the array while also strengthening and preventing torsional motion in the array. This allows for more control over the final placement of the magnetic compression anastomosis device and prevents an undesired geometry from forming.

Figure 25:
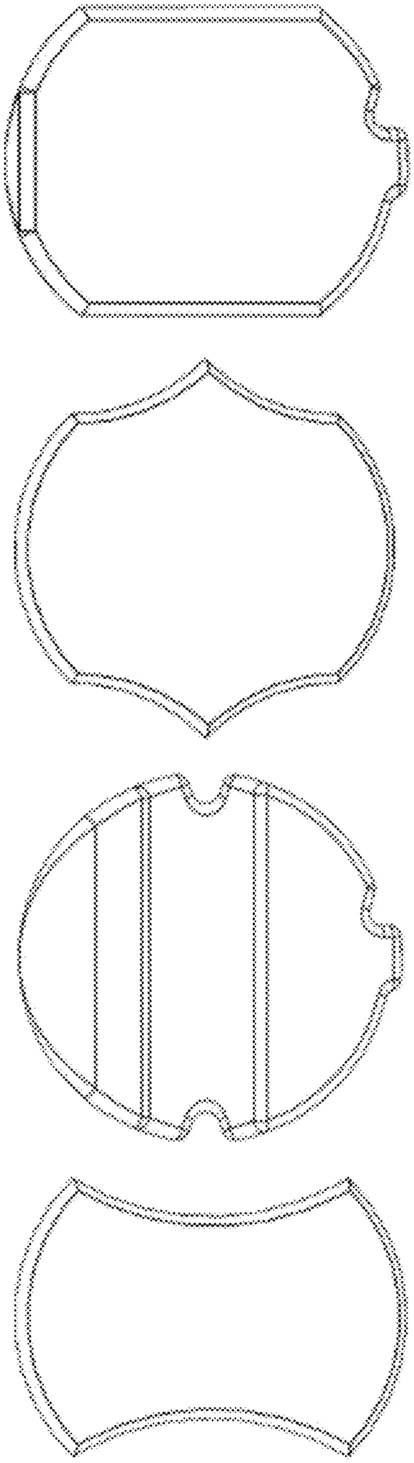
FIG. 25 shows profiles of various geometries of magnetic segments in accordance with certain embodiments.

Various profiles of various geometries of magnetic arrays are possible with the vertebrae 101 of the present invention, as is shown in FIG. 25. For example, the vertebra skin 102 can include smooth and/or patterned features and can be configured with different outer geometries such as to accomplish different anastomosis goals. For example, geometry (a) has concave sides, geometry (b) has convex sides with notches, geometry (c) has pointed side protrusions that could assist with cutting tissue, and geometry (d) has flat sides that could compress and necrose a larger area of tissue. The vertebrae 101 can include other features such as various types of protrusions or recesses, e.g., to help secure the device 100 to tissue. All vertebrae could use the same geometry, or different vertebrae could use different geometries.

It should be noted that, while the flex element 106 is encapsulated underneath the vertebra skin in the embodiments described above, alternative embodiments could place the flex element(s) 106 on the outside of the vertebra skin.

Figure 26:
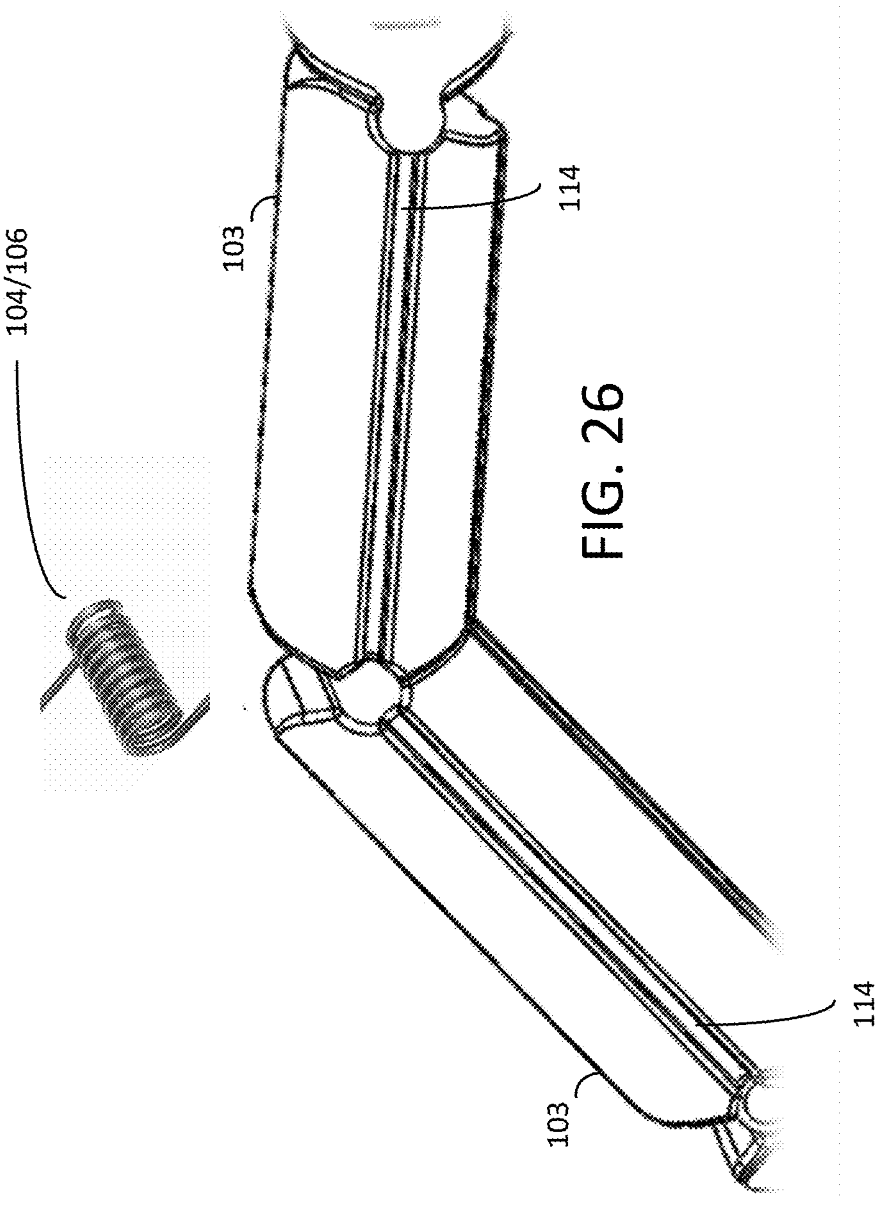
FIG. 26 shows an example of a roller in the form of a torsion spring in accordance with certain embodiments.

It should be noted that, while two example flex elements 106 are shown and described herein, the present invention is not limited to these or to any particular flex element(s). For example, a flex element could include a coil spring. In some embodiments, a spring (e.g., a coil spring or a torsion spring) could act as both the roller and the flex element, for example, as depicted schematically in FIG. 26. In some embodiments, a single flex element may span multiple magnet segments.

Figure 27:
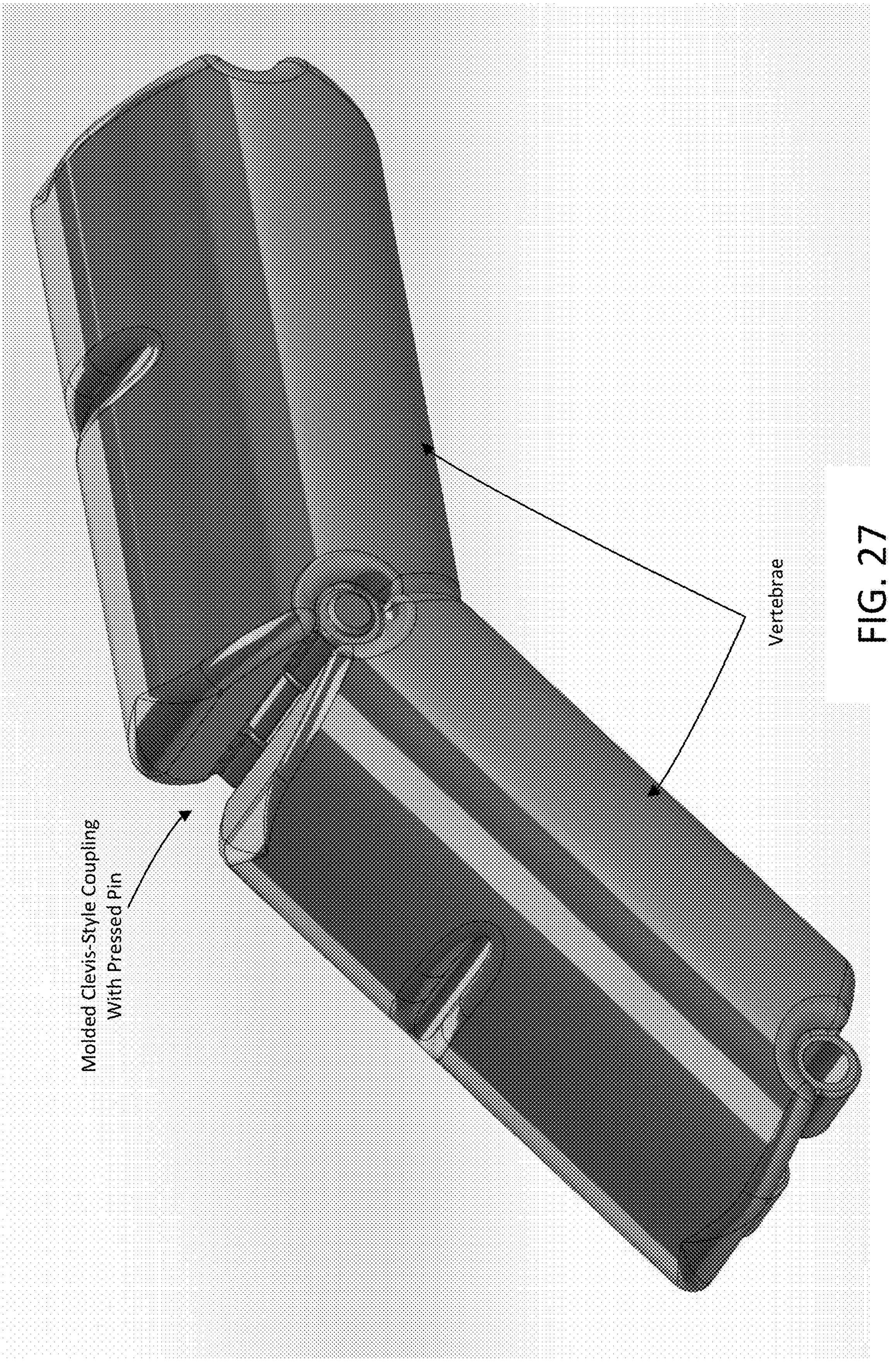
FIG. 27 depicts a portion of a magnetic compression anastomosis including two over-molded multipiece vertebrae connected by a clevis-style coupling in accordance with certain embodiments.
Figure 28:
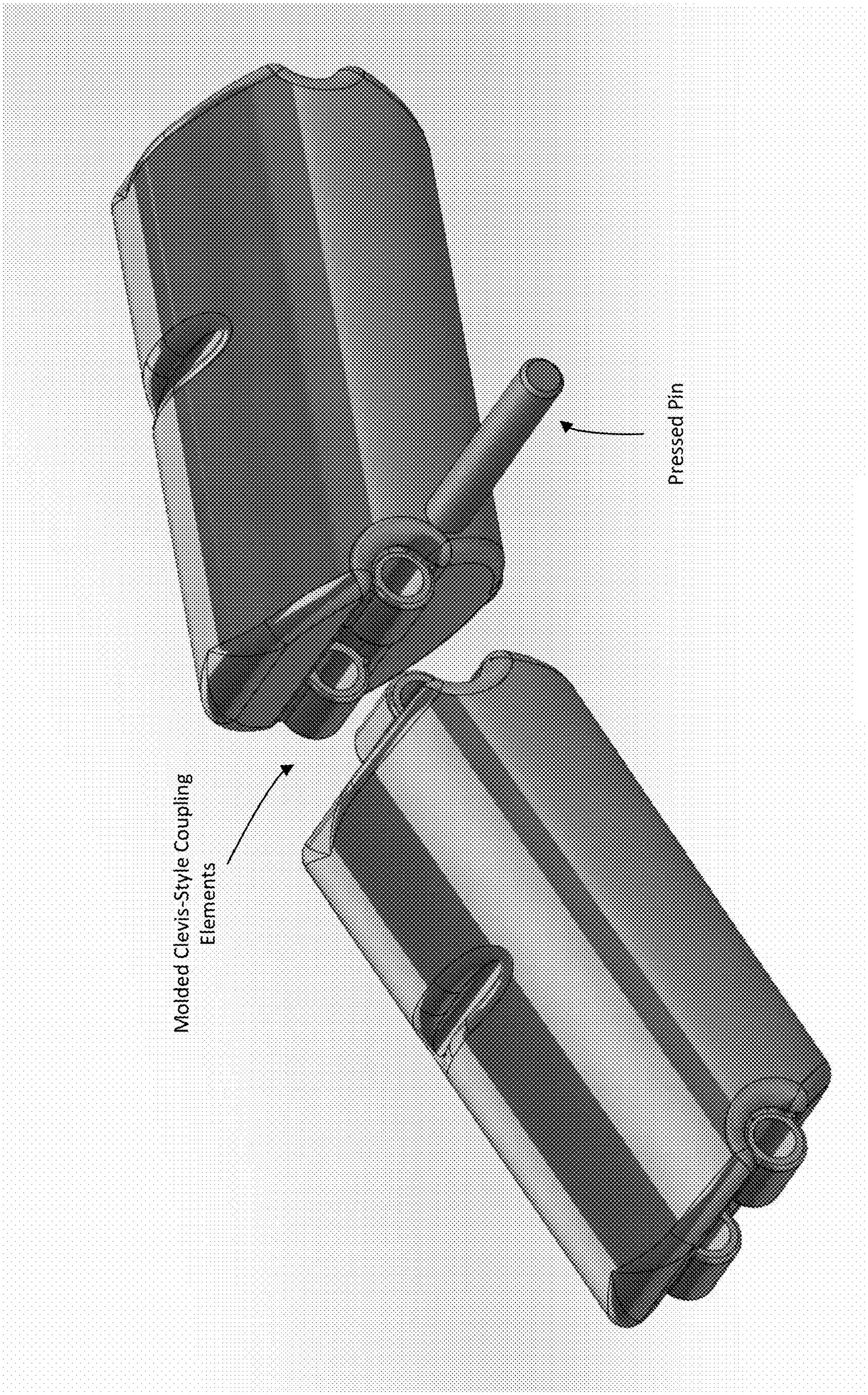
FIG. 28 shows an exploded view of the device of FIG. 27 showing the molded clevis-style coupling elements and the pressed pin used to connect the two vertebrae.
Figure 29:
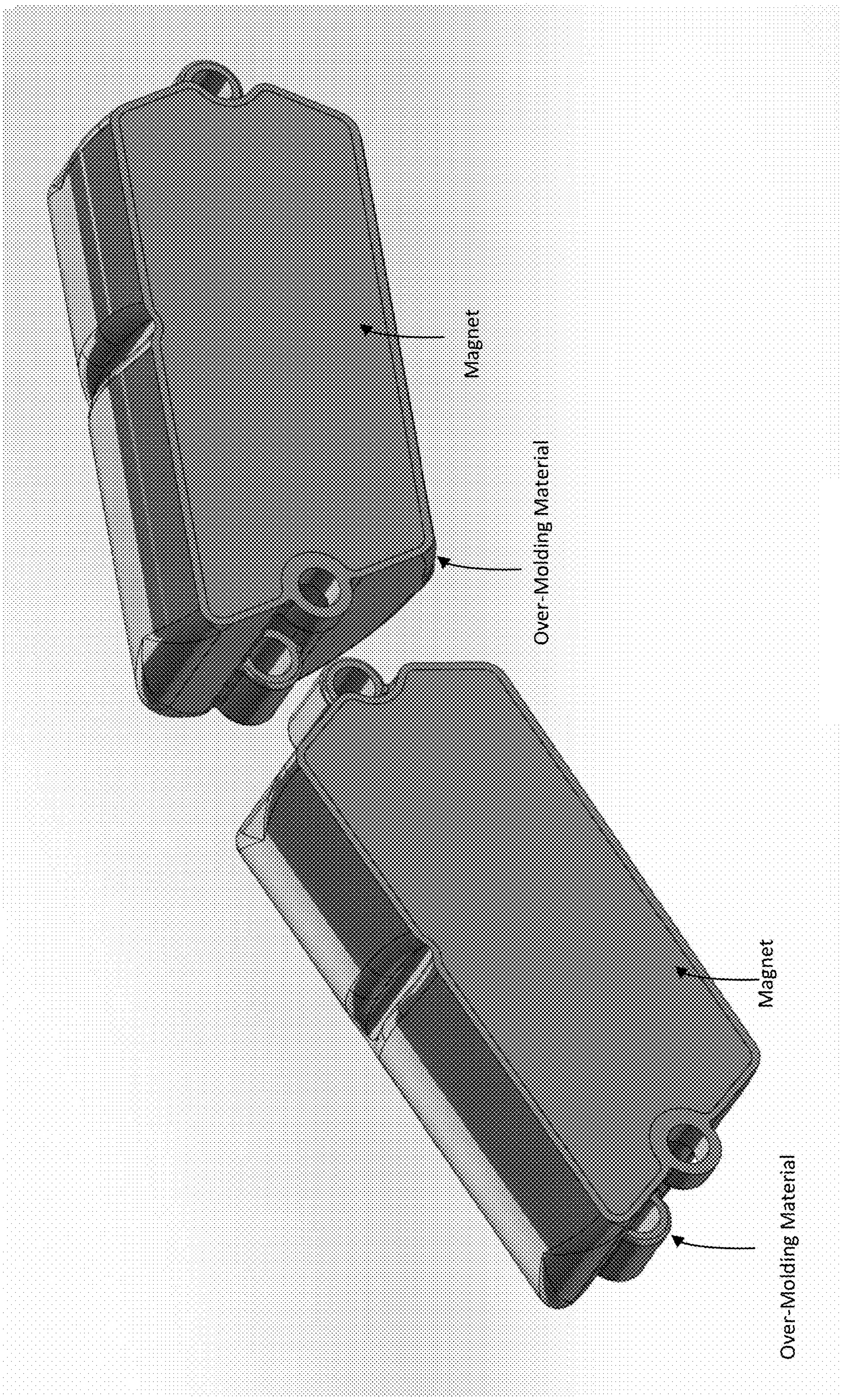
FIG. 29 depicts a cross-sectional view of the device of FIG. 28 showing the magnets with polymer over-molding to cover the magnets and form the clevis-style coupling elements.
Figure 30:
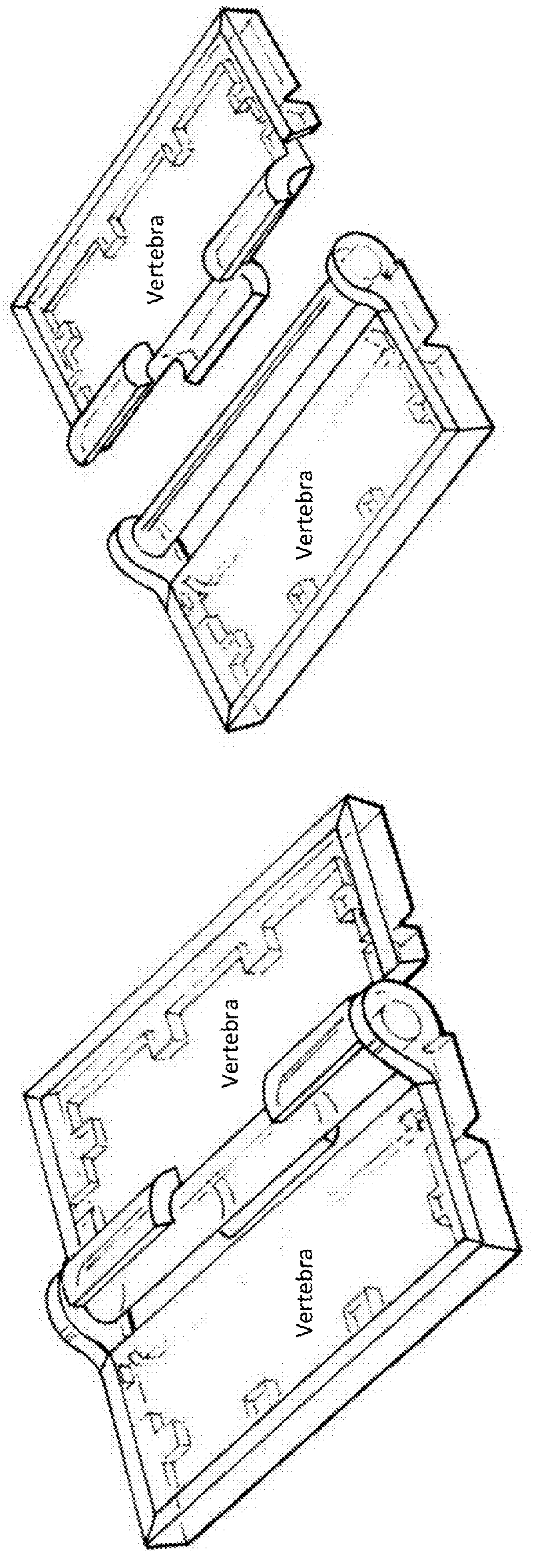
FIG. 30 is a schematic diagram depicting a first type of snap-fit coupling (hinge).
Figure 31:
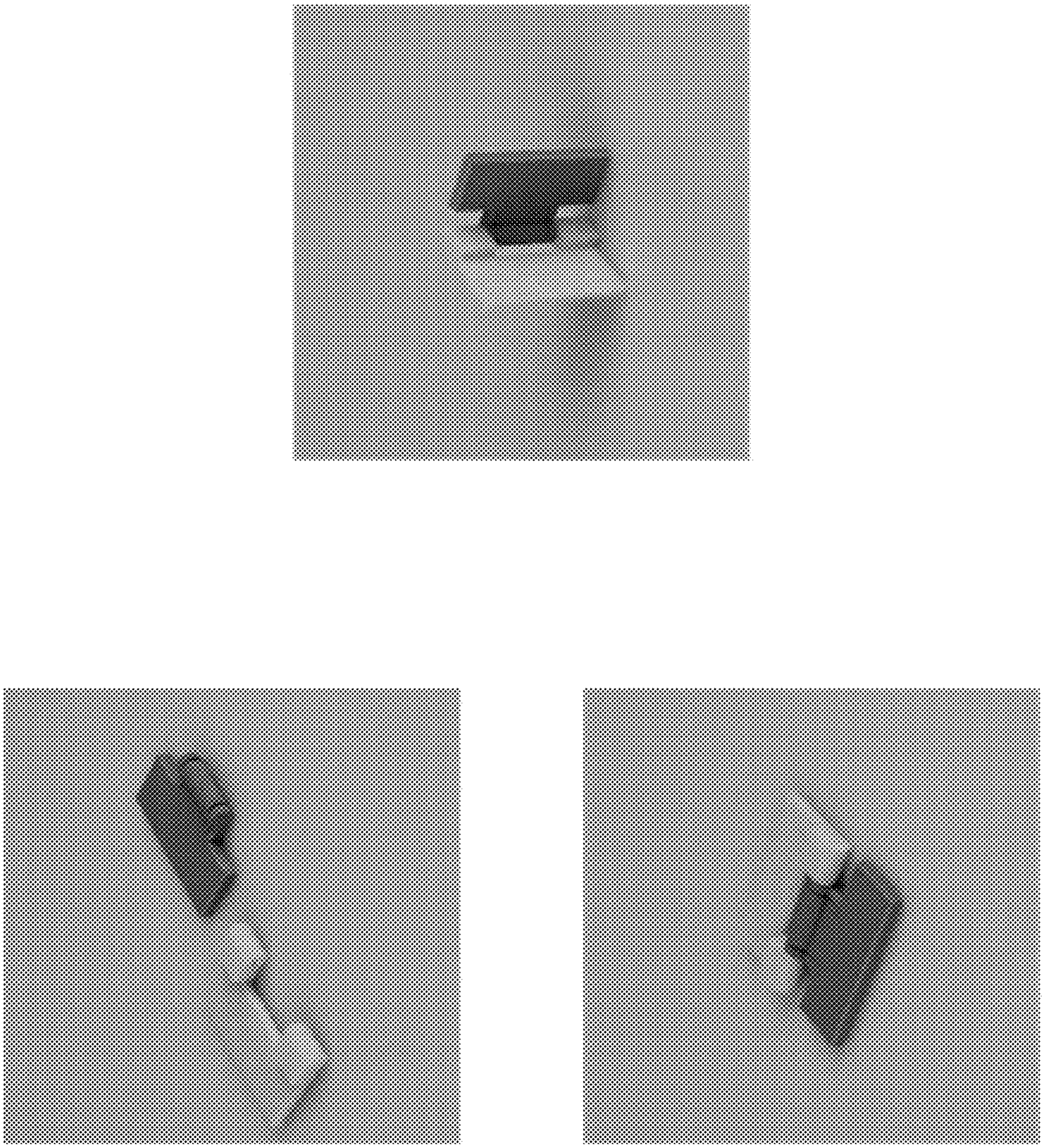
FIG. 31 is a schematic diagram depicting a second type of snap-fit coupling (hinge).
Figure 32:
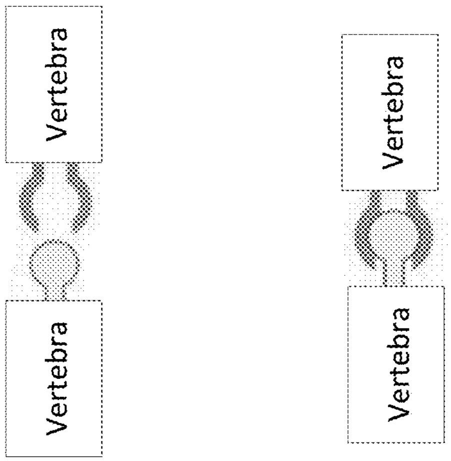
FIG. 32 is a schematic diagram depicting a third type of snap-fit coupling (hinge).

FIGS. 27-29 depict a magnetic compression anastomosis device with over-molded multipiece vertebrae in accordance with another embodiment. FIG. 27 depicts a portion of a magnetic compression anastomosis including two over-molded multipiece vertebrae connected by a clevis-style coupling (e.g., a clevis joint) in accordance with certain embodiments. FIG. 28 shows an exploded view of the device of FIG. 27 showing the molded clevis-style coupling elements and the pressed pin used to connect the two vertebrae (in this embodiment, the pressed pin is a solid pin, although in alternative embodiments the pressed pin may be a hollow cylinder or other appropriate configuration. FIG. 29 depicts a cross-sectional view of the device of FIG. 28 showing the magnets with over-molding (e.g., in which the vertebra skin is an over-molded vertebra skin) to cover the magnets and form the clevis-style coupling elements. In this embodiment, the magnetic compression anastomosis device uses magnetic coupling between the two vertebrae to transition from a linear delivery configuration to a circular or polygonal deployed configured (i.e., without mechanical elements such as one or more flex elements 106 or a spring roller), although alternative embodiment could additionally or alternatively include mechanical elements (e.g., one or more flex elements 106 or a spring roller) to cause or facilitate the transition from delivery configuration to deployed configuration. Mechanical element(s) could be embedded within and/or over-molded by the over-molding material (e.g., one or more flex elements 106 could be secured by the over-molding material). The over-molding material may be any appropriate material such as a polymer or composite material. Also, it should be noted that the vertebra skin could be formed without over-molding around the magnet, e.g., forming a shell and then inserting the magnet into the already-formed shell, such as a shell formed by injection molding, machining, etc. It also should be noted that embodiments are not limited to clevis-style couplings but instead could use other types of coupling that allow the two vertebrae to transition from the linear delivery configuration to the deployed configuration, e.g., a pin-less coupling such as a snap-fit coupling (e.g., hinge) of the types depicted schematically in FIGS. 30-32 or a ball-and-socket joint (where certain couplings can be characterized as having a male feature on one vertebra that connects with a corresponding female feature on another vertebra). In the described example, the coupling elements are formed as part of the molding process, although the coupling elements could be formed in other ways (e.g., machining the coupling elements after formation of the shell, or attaching coupling elements to the shell). It should be noted that, in embodiments having a cylindrical roller element (e.g., a hollow cylinder or solid cylinder), the cylindrical roller element may be integral to the magnet, the vertebra skin, or the molded shell.

It should be noted that, in embodiments having one or more flex elements, the flex element(s) may be part of the roller (e.g., a cylinder, torsion spring, or nitinol roller with flex arms formed integrally with or added to the roller such as by soldering or welding or other attachment) or may be part of the vertebra skin/shell.

Generally speaking, as described herein, the couplings between vertebrae preferably restrict movement/rotation to a single plane to help with the transition from the delivery configuration to the deployed configuration.

It should be noted that, in certain embodiments, a magnetic compression anastomosis device with multipiece vertebra can be provided within a delivery device such as a catheter, endoscope, laparoscope, trocar, needle, or other delivery device and therefore the delivery device in combination with the device 100 can be considered an embodiment of the invention.

Embodiments also can include methods of manufacturing the device 100 such as by providing the various components (e.g., magnets, rollers, flex elements, and vertebra skins), positioning a roller and flex element between two magnets and securing them as needed (e.g., securing the flex element within magnet channels), and placing a vertebra skin over the magnet, roller, and flex element.

It should be noted that kits can be provided with magnets, rollers, flex elements, and different types of vertebra skins having different configurations that can be used for different types of anastomosis procedures such that different devices 100 can be prepared, e.g., depending on the amount and type of pressure needed for a particular procedure, the location of the procedure, and the size of the anastomosis to be created.

It should be noted that self-assembling magnetic anastomosis addresses several of the historical disadvantages of traditional anastomosis such as allowing a surgical-quality anastomosis in a minimally-invasive fashion using devices that reproducibly re-assemble into a larger magnet structure of a predetermined shape in vivo. The constraints imposed by the described embodiments are designed to allow the devices to consistently self-assemble into the correct shape upon deployment, which greatly reduces the risks of surgical complications due to misshapen devices or premature detachment and also reduces the risks associated with surgical access and ensure that the anastomosis is formed with the correct geometric attributes. Overall, this ensures the patency of the anastomosis.

Thus, as described herein, embodiments include flexible linear magnetic devices comprising linked magnetic multipole segments that, when extruded from the end of a deployment channel or lumen, self-assemble to form a rigid, multipolar polygonal ring magnet (PRM; generally "magnetic device"). The self-assembly is directed by the configuration of magnets, rollers, flex elements, and vertebra skins that is capable of returning to a pre-determined shape. Generally speaking, the physical and magnetic structure of the deployed magnetic devices is such that when two magnetic devices approach one another, there is a rapidly strengthening attractive magnetic interaction, which creates a coupling between the magnetic devices. In some instances, it is necessary to pre-align the complimentary devices, however, in other instances the devices self-align by undergoing fast in-plane rotation with respect to one another, as discussed in detail below. As described in detail below, systems including the magnetic devices may include an endoscope having sensors that allow the endoscope to sense the position of a mating magnetic device or another endoscope that will deploy the mating device.

When deployed in adjacent tissues, for example adjacent organs or different regions of the same organ, the coupled magnetic devices create a compressive ring that can be surgically opened, or allowed to form an anastomosis without further intervention. When paired devices are left alone, the compressive force against the tissues collapse the vasculature and extrude fluids in the tissues, further reducing the distance between the devices and increasing the magnetic attraction. With time, the coupled devices eventually couple completely and fall away, leaving a formed anastomosis. This cascade begins when the devices approach within "capture range," whereby their mutually-attractive forces are sufficient to align the devices, trap the intervening tissue, and resist the natural pliancy of the tissues as well as the motion of the tissue under normal physiologic function.

Overall, the design specifications of the devices depend on the patient and the intended anastomosis. The design specifications may include: required capture range, desired effective inner and outer diameters of the deployed polygonal rings (e.g., as defined by the desired anastomosis size and instrument passage), thickness of the target tissue, and the inner diameter of guiding channel and the smallest radius of curvature to which the guiding channel may be bent and through which the magnets must pass. Once the design specifications are chosen, corresponding magnetic device designs can be determined, such as polygon-side-count and length, and the maximum lateral dimensions of the flexible linear magnetic structure that will be deployed through the delivery instrument.

Deployment of a device 100 is generally illustrated in FIG. 1. When used with the techniques described herein, the devices allow for the delivery of a larger magnetic structures than would otherwise be possible via a small delivery conduit, such as in a standard endoscope, if the devices were deployed as a completed assembly. Larger magnet structures, in turn, allow for the creation of larger anastomoses that are more robust, and achieve greater surgical success. Because the magnetic devices are generally radiopaque and echogenic, the devices generally can be positioned using fluoroscopy, direct visualization (trans-illumination or tissue indentation), and ultrasound, e.g., endoscopic ultrasound. The devices can also be ornamented with radiopaque paint or other markers to help identify the polarity of the devices during placement. In some embodiments, the devices can be positioned by use of sensors located in proximity to the delivery lumen and able to sense the position of a mating device, e.g., using a Reed switch or a Hall-effect sensor.

Figure 2A:
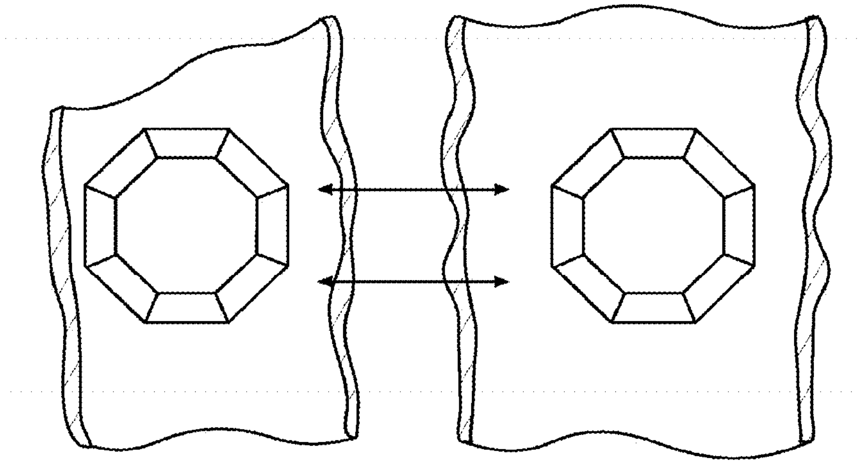
FIG. 2A shows magnet assemblies that have been delivered and deployed to adjacent tissues.
Figure 2B:
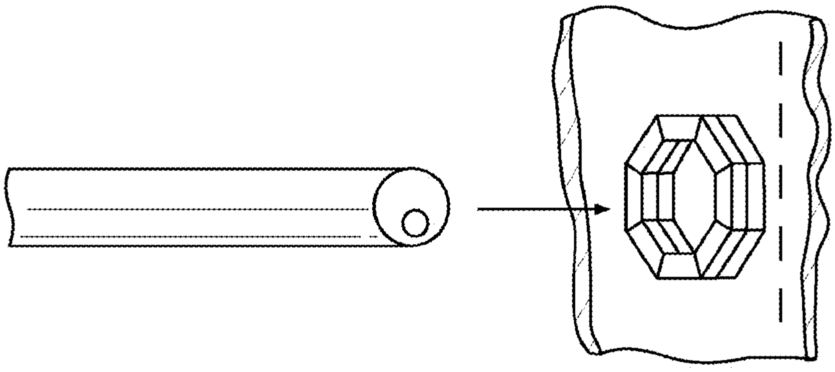
FIG. 2B shows the two magnet assemblies coupled together by magnetic attraction, capturing the intervening tissue. In some instances, the endoscope can be used to cut through the circumscribed tissue.

In general, as shown in FIG. 2A, a magnetic anastomosis procedure involves placing a first and a second magnetic structure adjacent to targeted tissues, thus causing the tissues to come together. The magnetic devices are generally deployed so that that opposite poles of the magnets will attract and bring the tissues together. The two devices may both be deployed inside the body, or one may be deployed inside the body and the other outside the body. Once the magnets have been deployed, the tissues circumscribed by the magnetic structures can be cut to provide an immediate anastomosis, as shown in FIG. 2B. In other embodiments, the tissues circumscribed by the devices will be allowed to necrose and degrade, providing an opening between the tissues. While the figures and structures of the disclosure are primarily concerned with annular or polygonal structures, it is to be understood that the delivery and construction techniques described herein can be used to make a variety of deployable magnetic structures. For example, self-assembling magnets can re-assemble into a polygonal structure such as a circle, ellipse, square, hexagon, octagon, decagon, or other geometric structure creating a closed loop. The devices may additionally include handles, suture loops, barbs, and protrusions, as needed to achieve the desired performance and to make delivery (and removal) easier.

As described with respect to the figures, a self-assembling magnetic anastomosis device can be placed with a number of techniques, such as endoscopy, laparoscopy, or with a catheter (e.g., not with direct visualization, fluoro, etc.). Regardless of method of device delivery, it is important to note that the procedure for creating the anastomosis can be terminated without perforation of tissue after confirmation of magnet coupling. As described previously, the compression anastomosis process can be allowed to proceed over the ensuing days, resulting in the natural formation of an opening between the tissues. The fused magnets can either be allowed to expel naturally or the magnets can be retrieved in a follow-up surgical procedure. Alternatively, if immediate bypass is required, the tissues circumscribed by the magnets can be cut or perforated. Perforation can be accomplished with a variety of techniques, such as cautery, microscalpel, or balloon dilation of tissue following needle and guidewire access.

Figure 3:
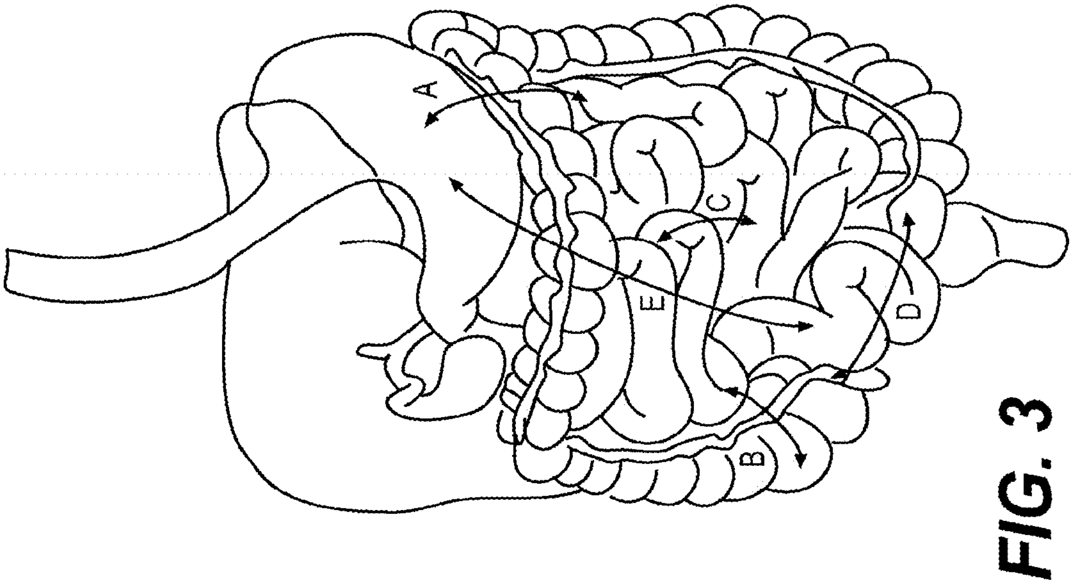
FIG. 3 shows several potential anatomical targets for anastomosis formation: Arrow A is stomach to small intestine, Arrow B is small intestine to large intestine, Arrow C is small intestine to small intestine, Arrow D is large intestine to large intestine, and Arrow E is stomach to large intestine.
Figure 4A:
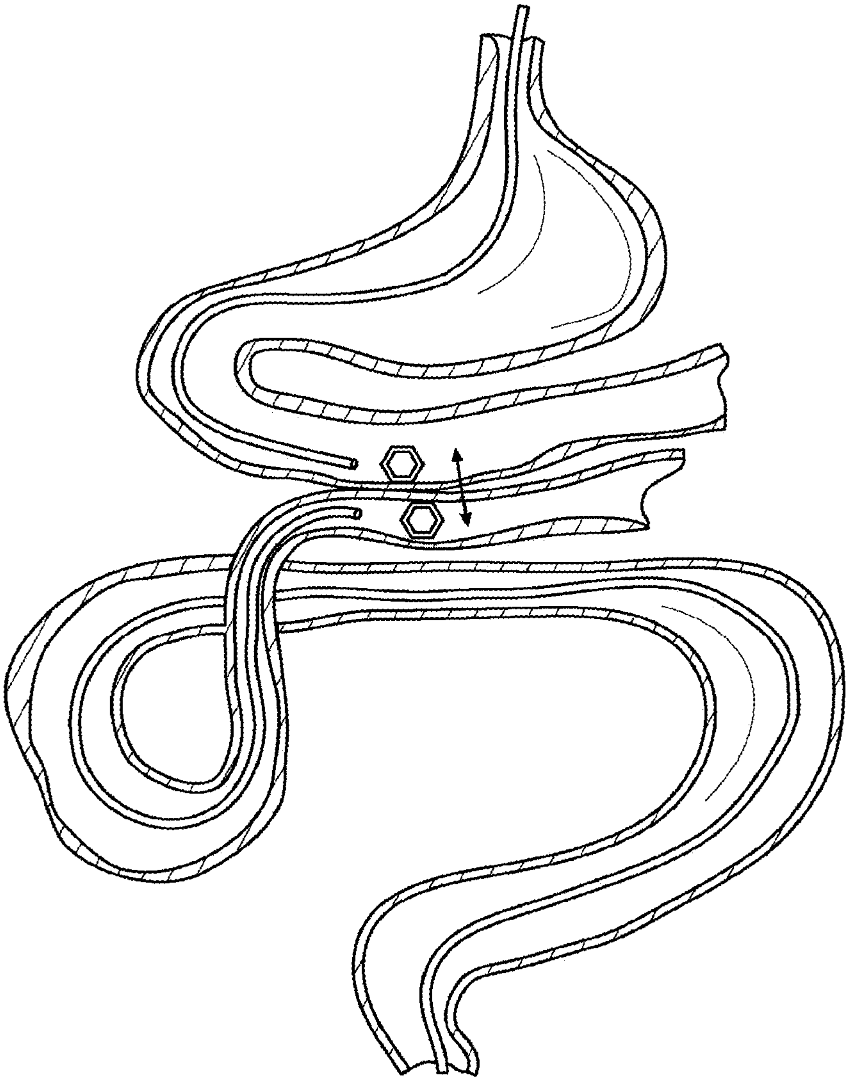
FIG. 4A shows one embodiment of delivery using two endoscopes (colonoscope and enteroscope or gastroscope) to deliver magnet assemblies.
Figure 4B:
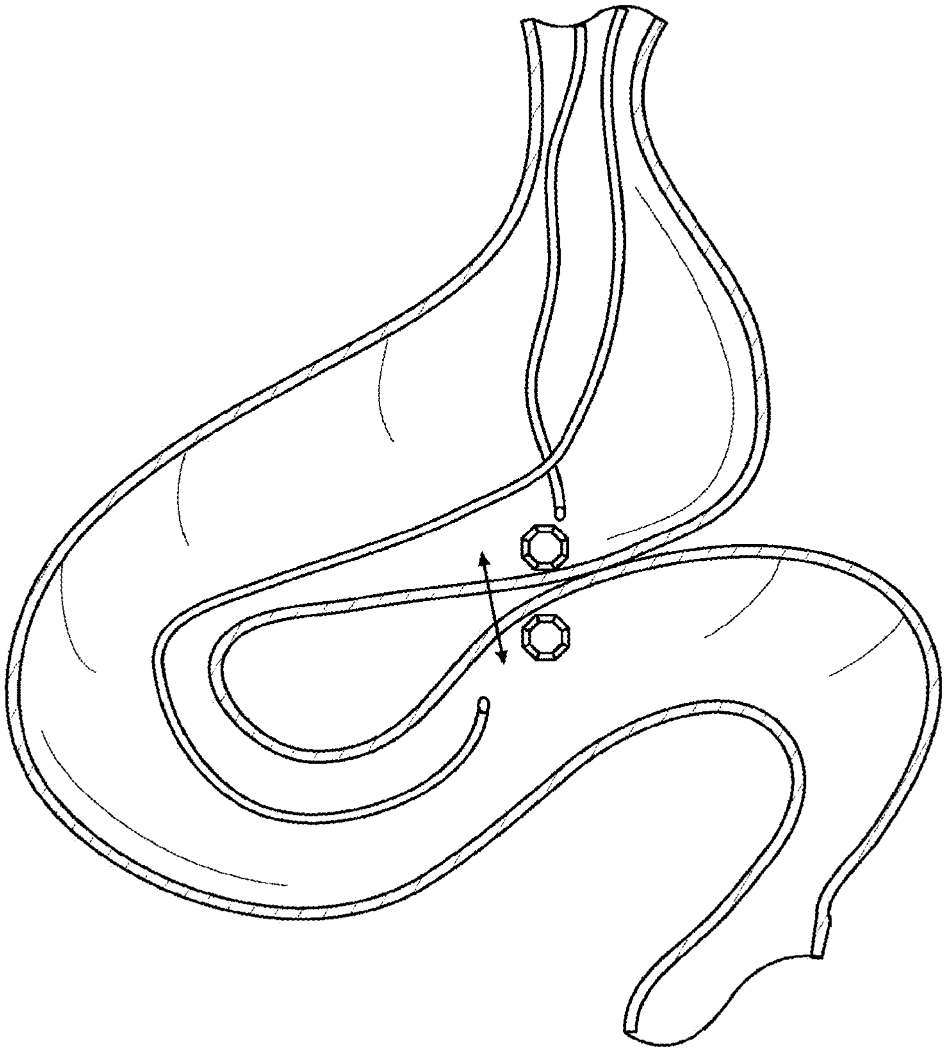
FIG. 4B shows another embodiment of delivery using two upper endoscopes both sharing per-oral entry to deliver magnet assemblies.
Figure 5:
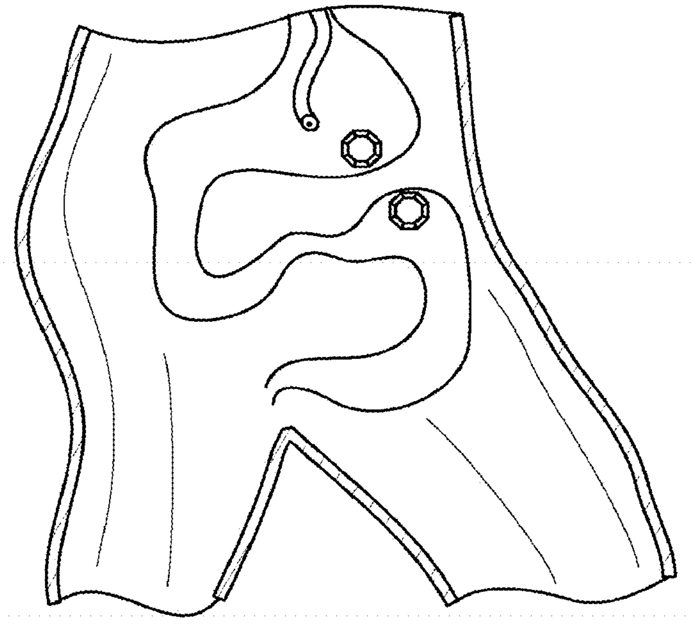
FIG. 5 shows another embodiment of delivery using a single endoscope to sequentially deliver magnet assemblies.

In some embodiments, the self-assembling magnetic devices are used to create a bypass in the gastrointestinal tract. Such bypasses can be used for the treatment of a cancerous obstruction, weight loss or bariatrics, or even treatment of diabetes and metabolic disease (i.e. metabolic surgery). Such a bypass could be created endoscopically, laparoscopically, or a combination of both. FIG. 3 illustrates the variety of gastrointestinal anastomotic targets that may be addressed with the devices of the invention: stomach to small intestine (A), stomach to large intestine (E), small intestine to small intestine (C), small intestine to large intestine (B), and large intestine to large intestine (D). In an endoscopic procedure, the self-assembling magnetic devices can be delivered using two simultaneous endoscopes, e.g., an upper endoscope or enteroscope residing in the upper small intestine, and a colonoscope residing in the lower small intestine, as shown in FIG. 4A. Alternatively, as shown in FIG. 4B, two simultaneous upper endoscopes (e.g., one residing in the stomach and the second in the small intestine) can be used to place the devices. In other embodiments, the self-assembling magnets can be delivered sequentially through the same endoscope, which has been moved between a first deployment position and a second deployment position. For example, in FIG. 4A, a single per-oral endoscope could deliver and deploy one self-assembling magnet in the small intestine, withdraw, and then deploy the second reciprocal magnet in the stomach. Again, magnet coupling could be confirmed using fluoroscopy. FIG. 5 illustrates removal of a single endoscope after placement of two magnetic devices.

A variety of techniques can be used to detect the first deployed magnetic device to assist placement of the second mating structure. Once the first device is deployed at the desired anastomotic location, the two deployed magnetic devices need to find one another's magnetic field so that they can mate and provide the compressional force needed to prompt formation of an anastomosis. Ideally, the devices can be roughly located within several cm of one another (e.g., using ultrasound), at which point the magnets should self-capture and self-align. Where this is not possible, other techniques such as one of the following techniques can be used. A first location technique involves a direct contact method using two endoscopes. Here an endoscope's displacement in an adjacent lumen creates a displacement seen by another endoscope in the adjacent lumen. The displacement identifies a potential intersection point for an anastomosis location. For example, a magnetic deployment tool (described below) will be deflected by the presence of a deployed device on the other side of a tissue wall.

The second location technique involves trans-illumination, whereby high intensity light from one endoscope is directed at the lumen wall of the proposed anastomosis site. Using this technique, another endoscope in the adjacent lumen looks for the light, which diffuses through the lumen wall and projects onto the wall of the adjacent lumen. This light represents the potential intersection anastomosis point. A cap or lens can also be placed over the light emitting endoscope to further intensify and pinpoint the proposed intersection point. A similar technique could use radio-wave- or ultrasound-transducers and receivers to collocate the endoscope tips. In some embodiments, a system may include an endoscope having a sensor and a magnetic anastomosis device for deployment using the endoscope.

A third location technique involves magnetic sensing techniques to determine the proximity of the deployed ring magnet in the adjacent lumen. By maximizing the magnetic field being sensed, the minimum distance between the adjacent channels can be identified. The magnetic sensor can be carried on a probe inserted down the working channel of the endoscope and utilize common magnetic sensing technology such as a Hall Effect Sensor or Reed switch.

With trans-illumination and magnetic sensing, an additional accessory may also assist with delivering magnetic devises to a precise anastomosis site. A radially expanding ring structure can be deployed with the endoscope or laparoscope that can press fit and seat itself on the scope's outer diameter. The outer diameter of this expanding element is sized to allow the deployed device to seat itself on this expanding element (again likely a press fit). With this expanding element and magnetic device radially seated about the endoscope axis, the endoscope can be directed to the ideal anastomotic location through direct contact, trans-illumination, or magnetic sensing, and then the mating magnet device released when the anastomosis site is identified.

Figure 6:
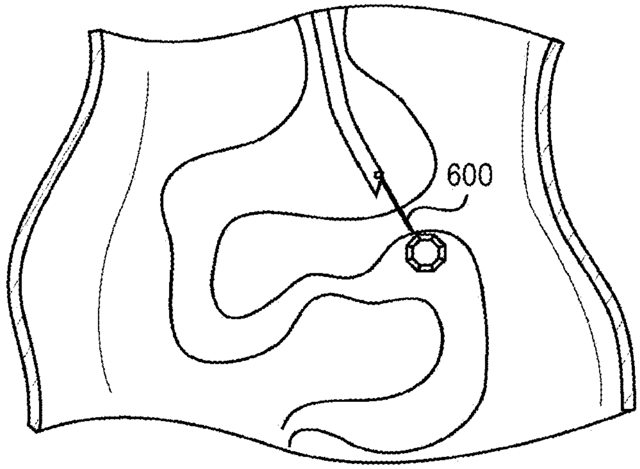
FIG. 6 shows another embodiment of delivery using endoscopic ultrasound guided needle delivery of one magnet assembly into lumen #1 followed by deployment to of the second magnet assembly in lumen #2.

In other embodiments, the self-assembling magnet devices could be delivered using ultrasound guidance, e.g., endoscopic ultrasound. For example, using an echoendoscope in the stomach, a suitable small intestine target could be identified. As shown in FIG. 6, a delivery needle 600 (e.g., an aspiration needle) or catheter can be used to access to the small intestine target and deliver the self-assembling magnets into the small intestine lumen. The delivery can be guided with fluoroscopy or endoscopic ultrasound. Following self-assembly, these small intestine magnets would couple with a second set of magnets deployed in the stomach. The two devices can be delivered with the same needle or with different needles. It is also possible to deliver the first device with an endoscope and the second device with a needle or vice versa.

Figure 7:
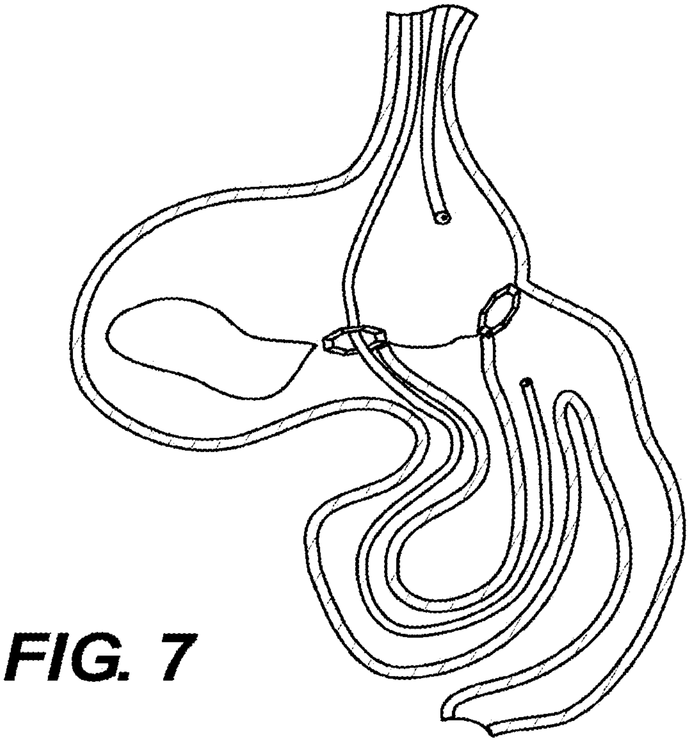
FIG. 7 shows the creation of a preliminary anastomosis to serve as a conduit for deeper endoscope delivery in order to create subsequent multiple anastomoses.

In another embodiment, illustrated in FIG. 7, a first anastomosis, created in an initial procedure, can be used to provide access for the creation of a second anastomosis. This process could theoretically be repeated multiple times to create additional anastomoses. For example, a gastrojejunal anastomosis (stomach to mid-small intestine) could serve as a conduit for the creation of a second, more distal gastrojejunal anastomosis. Ultimately, in this particular scenario, the stomach would have several bypasses to the small intestine. Additionally, in some instances, more anastomoses could be added to "titrate" to a specific clinical effect (e.g., lower glycosylated hemoglobin in type 2 diabetes). In alternative embodiments, an anastomosis may be placed to give access for a different type of surgery, e.g., tumor removal.

Figure 8:
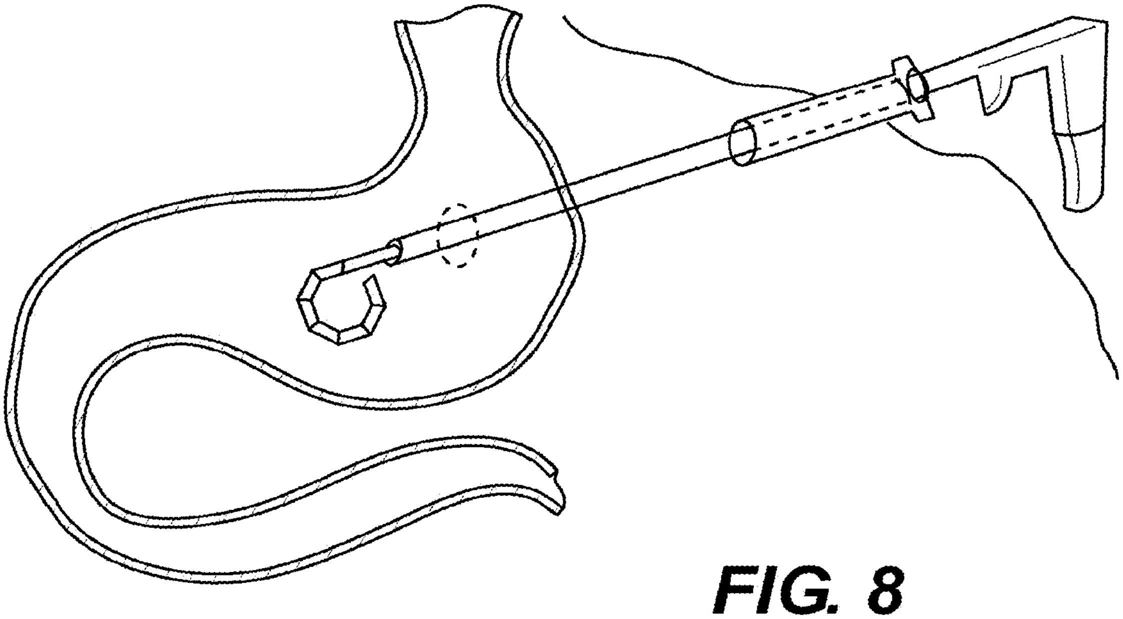
FIG. 8 shows laparoscopic magnet device delivery into a lumen (stomach, in this example).

In another embodiment of delivery, the self-assembling magnets could be delivered laparoscopically through a surgical incision into the target organs (e.g., stomach and small intestine) and allowed to couple to create an anastomosis, as shown in FIG. 8. Again, this procedure could be directed with fluoroscopy or ultrasound and the procedure can be purely laparoscopic, or a combination of endoscopic and/or laparoscopic and/or needle procedures.

Gastrointestinal anastomoses of different configurations can be used to address a number of conditions resulting in either partial or complete bypasses. An anastomosis or series of anastomoses between any segment or segments of the gastrointestinal tract (e.g., esophagus, stomach, small bowel, colon or rectum) may be necessary as part of surgical treatment of different cancers, Crohn's disease, colitis, stricture resection, repair or retreatment of prior surgery or emergent repair of a critical wound. An anastomosis or series of anastomoses between the proximal bowel and distal bowel may be used for treatment of obesity and metabolic conditions, such as Type II diabetes and dyslipidemia. The procedure can also be used to induce weight loss and to improve metabolic profiles, e.g., lipid profiles. The bowel includes any segment of the alimentary canal extending from the pyloric sphincter of the stomach to the anus. In some embodiments, an anastomosis is formed to bypass diseased, mal-formed, or dysfunctional tissues. In some embodiments, an anastomosis is formed to alter the "normal" digestive process in an effort to diminish or prevent other diseases, such as diabetes, hypertension, autoimmune, or musculoskeletal disease. It is understood that anastomoses can be configured in several different manners (e.g., side-to-side, end-to-end, side-to-end).

Using the self-assembling magnetic devices as discussed herein, it is possible to create a side-to-side anastomosis that does not require exclusion of the intermediate tissues, as is common with state-of-the-art bariatric procedures. That is, using the devices of the invention (or other means for creating an anastomosis) it is possible to create an alternate pathway that is a partial bypass for fluids (e.g., gastric fluids) and nutrients (e.g., food), while at least a portion of the old pathway is maintained. This design allows the ratio of "normal" to "modified" digestion to be tuned based upon the goals of the procedure. In other words, using the described procedure, a doctor can choose the ratio of food/fluids shunted down the new (partial) bypass versus food/fluids shunted down the old pathway. In most instances, the fraction shunted down the bypass limb will drive the patient toward the desired clinical endpoint (e.g., weight loss, improvement in glycosylated hemoglobin, improvement in lipid profile, etc.) The mechanism by which the endpoints are achieved may involve early macronutrient delivery to the ileum with stimulation of L-cells and increase in GLP-1 production, for example. The mechanism may also involve loss of efficiency of nutrient absorption, especially glucose, thereby reducing blood glucose levels. At the same time, however, the fraction shunted down the old pathway protects against known metabolic complications that can be associated with bariatric surgery such as excessive weight loss, malabsorptive diarrhea, electrolyte derangements, malnutrition, etc.

To achieve a desired ratio of bypass (e.g., re-routing food and secretions to flow down the new pathway, say, 70% or 80% or 90% or 100% of the time), the size, location, and possibly number of anastomoses will be important. For example, for a gastrojejunal anastomosis, it may be critical to place the anastomosis in a dependent fashion to take advantage of the effects of gravity. Also, instead of a round anastomosis, it may be better to create a long, oval-shaped anastomosis to maximize anastomotic size. Alternatively, multiple gastrojejunal anastomoses may be used to titrate to a certain clinical endpoint (e.g., glycosylated hemoglobin in Type II diabetes). Most of the procedures described herein may be used to place one or more anastomoses, as needed, to achieve the desired clinical endpoint. For example, the two endoscope procedures illustrated in FIGS. 4A and 4B can be used to create a partial bypass of a portion of the bowel. Based upon the desired ratio of bypassed and non-bypassed nutrients, the anastomoses shown in FIGS. 4A and 4B can be made larger, e.g., greater than 1 cm in open diameter, or several smaller anastomoses can be placed to achieve the desired ratio.

The procedure is also adjustable. For example, a first anastomosis may be formed and then, based upon clinical tests performed after the procedure, one or more anastomoses can be added to improve the results of the clinical tests. Based upon later clinical results, it may be necessary to add yet another anastomosis. Alternatively, it is possible to partially reverse the condition by closing one or more anastomosis. Because the partially bypassed tissues were not removed, they can return to near normal functionality with the passage of greater amounts of nutrients, etc. The anastomoses may be closed with clips, sutures, staples, etc. In other embodiments, a plug may be placed in one or more anastomoses to limit the ratio of nutrients that traverse the "normal" pathway. Furthermore, it is possible to close an anastomosis in one location in the bowel and then place a new anastomosis at a different location. Thus, is possible to generally and tunably create partial bypasses, or a series of partial bypasses, between portions of the bowel to achieve clinical endpoints, e.g., as described in FIG. 3.

The described procedures may also be used with procedures that remove or block the bypassed tissues, as is common with bariatric procedures. For example, a gastrojejunal anastomosis may be coupled with a pyloric plug (gastric obstruction) or another closure of the pylorus (e.g., sutured closure) to shunt food completely down the new bypass. Such procedures can be used, for example, to bypass tissue that is diseased, e.g., because of cancer.

In another category of procedures, endoscopic ultrasound (EUS) can be used to facilitate guided transgastric or transduodenal access into the gallbladder for placement of a self-assembling magnetic anastomosis device. Once gallbladder access is obtained, various strategies can be employed to maintain a patent portal between the stomach and the gallbladder or the duodenum and the gallbladder. In another embodiment, gallstones can be endoscopically retrieved and fluid drained. For example, using the described methods, an anastomosis can be created between the gallbladder and the stomach. Once the gallbladder is accessed in a transgastric or transduodenal fashion, the gallstones can be removed. Furthermore, the gallbladder mucosa can be ablated using any number of modalities, including but not limited to argon plasma coagulation (APC), photodynamic therapy (PDT), sclerosant (e.g., ethanolamine or ethanol).

Figure 9A:
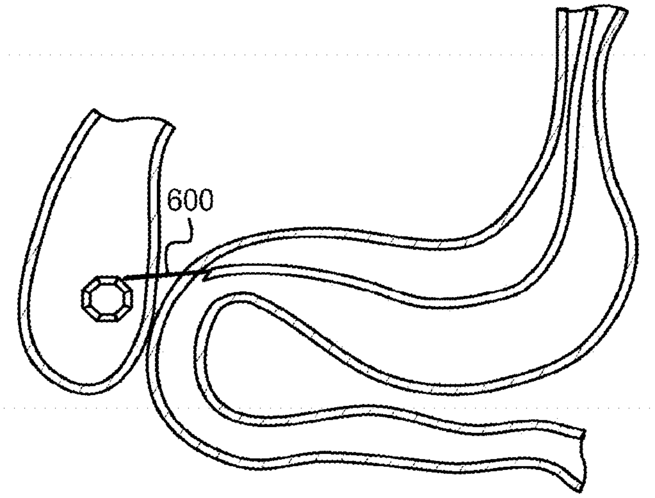
FIG. 9A shows endoscopic ultrasound guided needle delivery of a magnet assembly into the gallbladder which then couples with a second magnet assembly in the stomach or duodenum as shown in FIG. 9B.
Figure 9B:
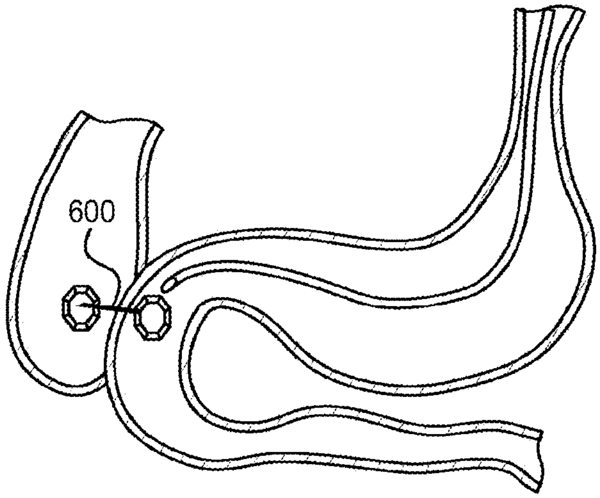

One strategy for creation of a portal is to deploy self-assembling magnets via an endoscopic needle under ultrasound guidance into the gallbladder and also into the stomach or duodenum. These magnets will mate and form a compression anastomosis or fistula. A second strategy for creation of a portal is to deploy self-assembling magnets via an endoscopic needle 600 as shown in FIGS. 9A and 9B. While the coupled magnetic assemblies are shown as octagons, the closed frame could take the shape of any polygonal structure, e.g., a square, a circle, a triangle, hexagon, heptagon, nonagon, decagon, dodecagon, etc. One such device would be deployed into the gallbladder, and the mating device would be deployed into the stomach or duodenum. In the same fashion as discussed above with respect to gastrointestinal deployment, the tissue circumscribed by the two magnetic devices can be cut with cautery, microscalpel, needle-knife, or other deployable cutting mechanism. In another embodiment, the coupled tissues can be left to necrose and form the anastomosis.

Figure 10:
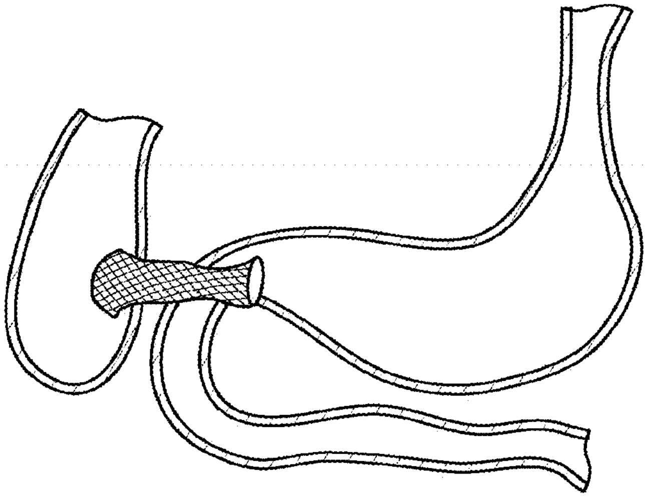
FIG. 10 shows stent deployment between the gallbladder and either the stomach or duodenum.
Figure 11:
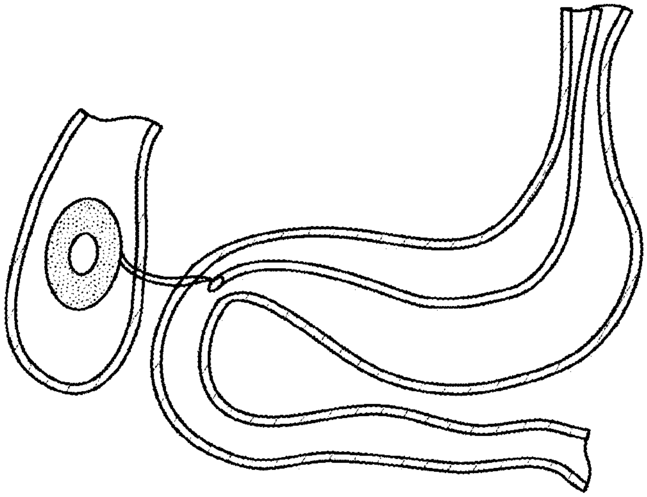
FIG. 11 shows another embodiment of an intra-gallbladder magnet assembly that is a balloon that fills with fluid, gas, or magnetic material. This balloon is tethered to the endoscope and is initially delivered through an endoscopic ultrasound guided needle.

The devices need not be limited to forming holes, however. Other structures can be coupled to one or more mating magnetic devices to created additional functionality. For example, a stent could be deployed between tissues, such as the gallbladder and the stomach, as shown in FIG. 10. Alternatively, the gallbladder magnet could be coupled to a balloon-based device that fills with air, fluid, magnetic pieces or magnetic particles. Upon inflation, the balloon would serve as an anchor in the bile duct following placement. The balloon could also have an annular configuration to allow for immediate access after coupling with the second magnet. Sec, e.g., FIG. 11. Regardless of embodiment, however, it is critical to contain the original access pathway within the confines of the coupled magnets, i.e., not leaving a pathway for the escape of bile. Otherwise, the opening will allow bile leakage that can result in peritonitis.

Another medical application for self-assembling magnets is direct biliary access. Currently, to achieve decompression for a malignant biliary stricture, endoscopic retrograde cholangiopancreatography (ERCP) is performed. The biliary tract is accessed endoscopically through the papilla in retrograde fashion and a stent is deployed across the stricture over a guidewire. These stents frequently require subsequent procedures for exchange, clean-out, or placement of additional overlapping stents. The need for exchange and cleaning is required to counteract the high rate of infection of the biliary tree (i.e. cholangitis) when using an ERCP procedure. Because of the high rate of morbidity, ERCP is typically limited to patients that have no other option to address pancreatic disease.

Using devices of the invention, however, it is possible to easily form an anastomosis between the bile duct (preferably the main bile duct) and either the duodenum or the stomach (choledocho-gastric and choledocho-duodenal anastomoses, respectively). This anastomosis is permanent and typically does not require intervention if located apart from the diseased tissue. In an embodiment, a biliary magnetic device is delivered directly into the bile duct under endoscopic ultrasound guidance. As described below, the self-assembling magnetic device is extruded through a needle or catheter, whereupon it deploys in the correct configuration. Using fluoroscopy or ultrasound, it is then possible to confirm that the device has self-assembled and is in the correct location. In some embodiments, the magnetic device may be tethered to the delivery needle or catheter by means of a detachable wire or suture to enable mechanical retraction until optimal positioning is confirmed.

Figure 12:
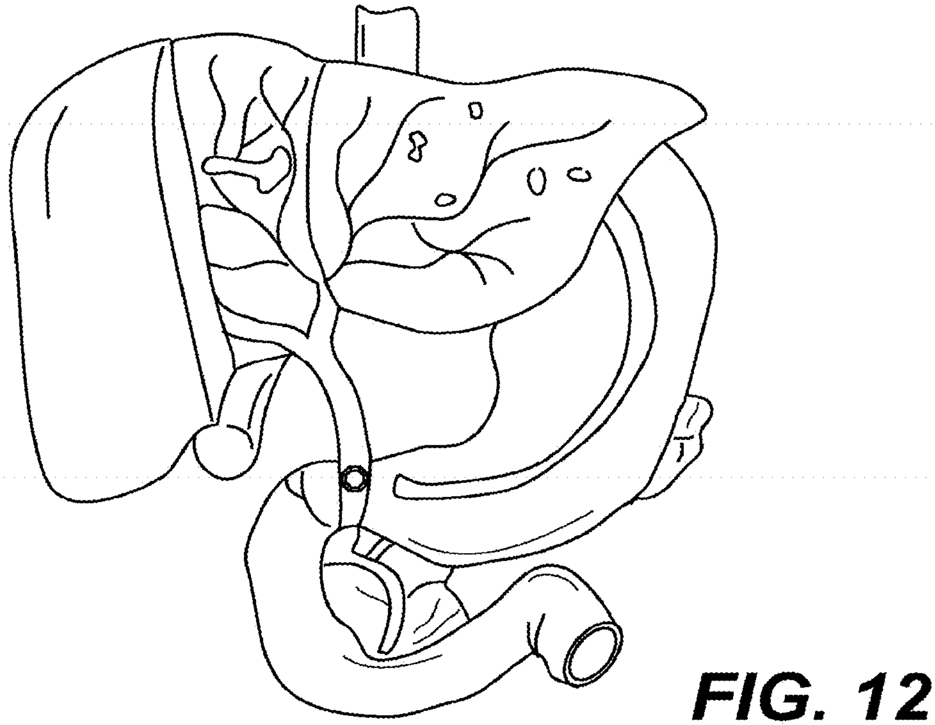
FIG. 12 shows endoscopic ultrasound guided needle delivery of a magnet assembly into the bile duct.
Figure 13:
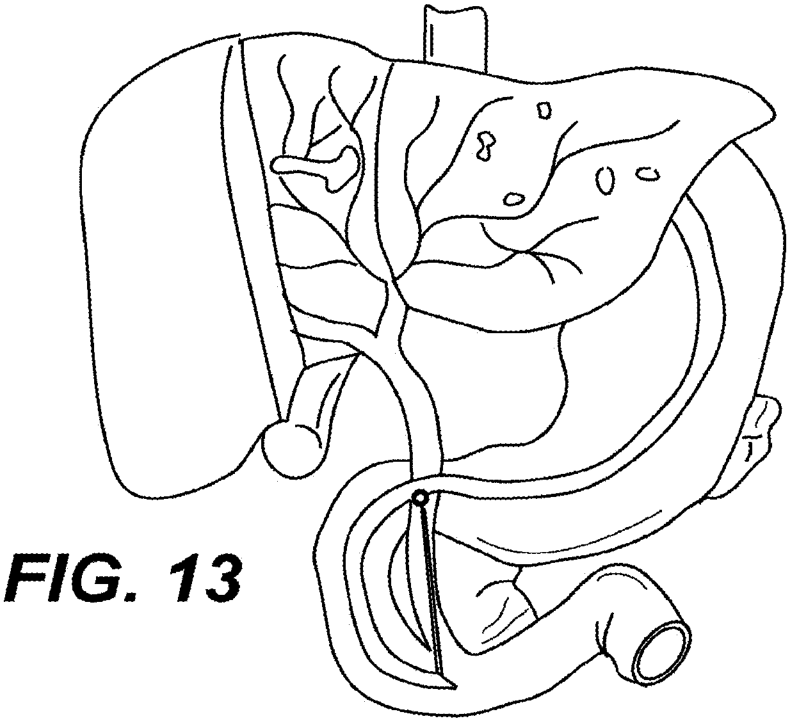
FIG. 13 shows magnet assembly delivery into the bile duct through endoscopic retrograde cholangiopancreatography techniques.
Figure 14:
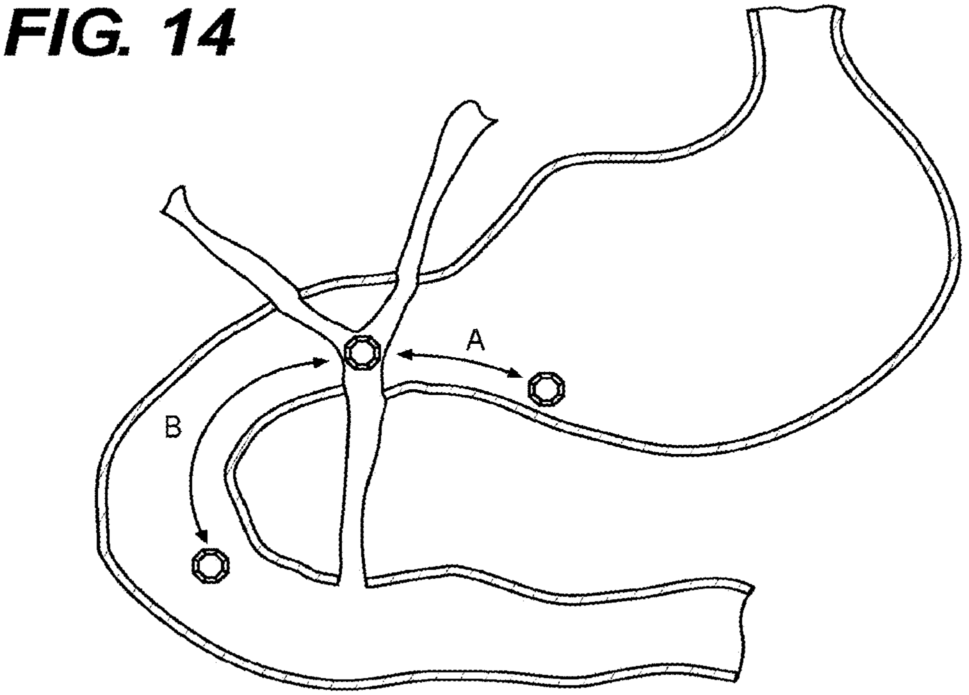
FIG. 14 shows coupling of the intra-bile duct magnet assembly with a second magnet assembly deployed either in the stomach (A) or duodenum (B).

In one embodiment, the magnetic device can be delivered endoscopically to the bile duct via wall of the duodenum, as shown in FIG. 12. In another embodiment, the biliary magnet can be delivered in conventional retrograde fashion through the ampulla into the bile duct, as shown in FIG. 13. One benefit of retrograde delivery is that it avoids needle punctures across tissue planes, as is the case with the deployment method shown in FIG. 12. Regardless of the method for delivering the biliary magnets, however, a second magnetic device is required in either the gastric (A) or duodenal (B) lumen, as shown in FIG. 14. Typically, this decision is dependent upon the patient's anatomy (e.g., size of the duodenal lumen) and the location of the initial biliary magnet. In scenarios based on endoscopic ultrasound needle delivery, the second magnetic device can be connected to the biliary magnet via the aforementioned detachable wire, and therefore extruded through the same delivery needle/catheter. Alternatively, the second device can be pre-attached to the exterior of the endoscope and slid into position for coupling after biliary magnet deployment. The latter procedure may be more applicable to forward-viewing echoendoscopes but may be used with endoscopes, generally.

Figure 15:
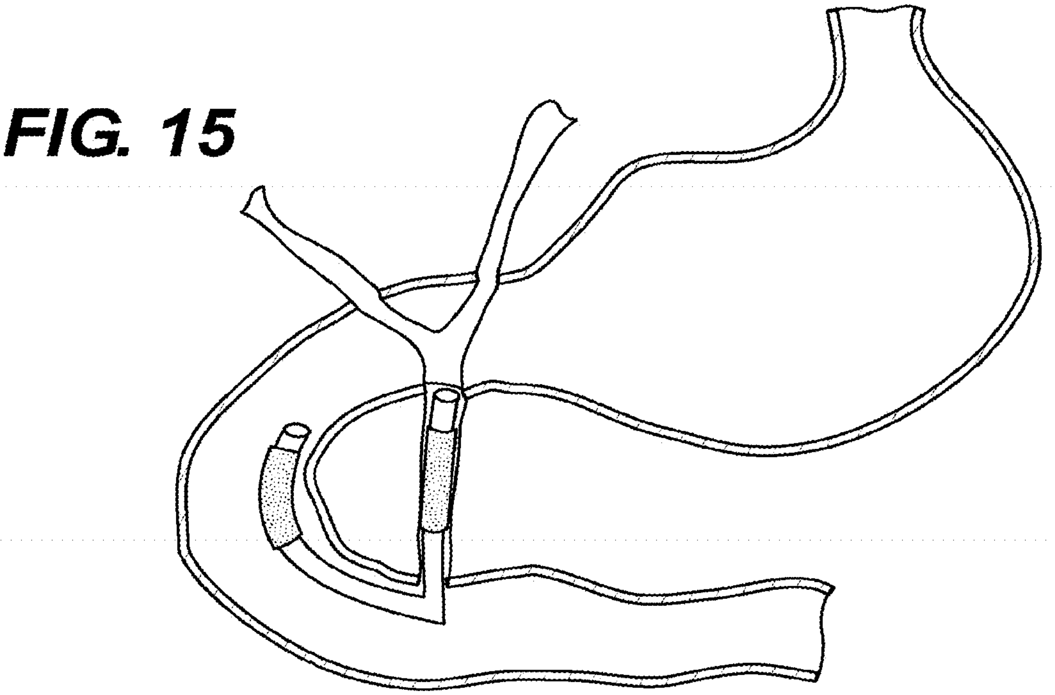
FIG. 15 shows another embodiment of bile duct magnetic anastomosis in which a hinged magnetic bile duct stent swings back onto itself by magnetic attraction to form an anastomosis between the bile duct and duodenum.

In another embodiment, the biliary magnet is a balloon-based device that fills with air, fluid, magnetic pieces or magnetic particles, similar to previously described with respect to gallbladder procedures. Upon inflation, the balloon would serve as an anchor in the bile duct following placement. In an embodiment, the balloon could have an annular configuration to allow for immediate access after coupling with the second magnet. Additionally, like the gallbladder procedures described above, a biliary magnetic device can be used with a stent form-factor. In an embodiment, the stent has an internal biliary magnet and a hinged external magnet. The stent can be inserted in retrograde fashion through the ampulla into the bile duct. The hinged external magnet can then be swung around and coupled with the internal biliary magnet to form a fistula between the bile duct and the duodenum, as shown in FIG. 15.

Figure 16:
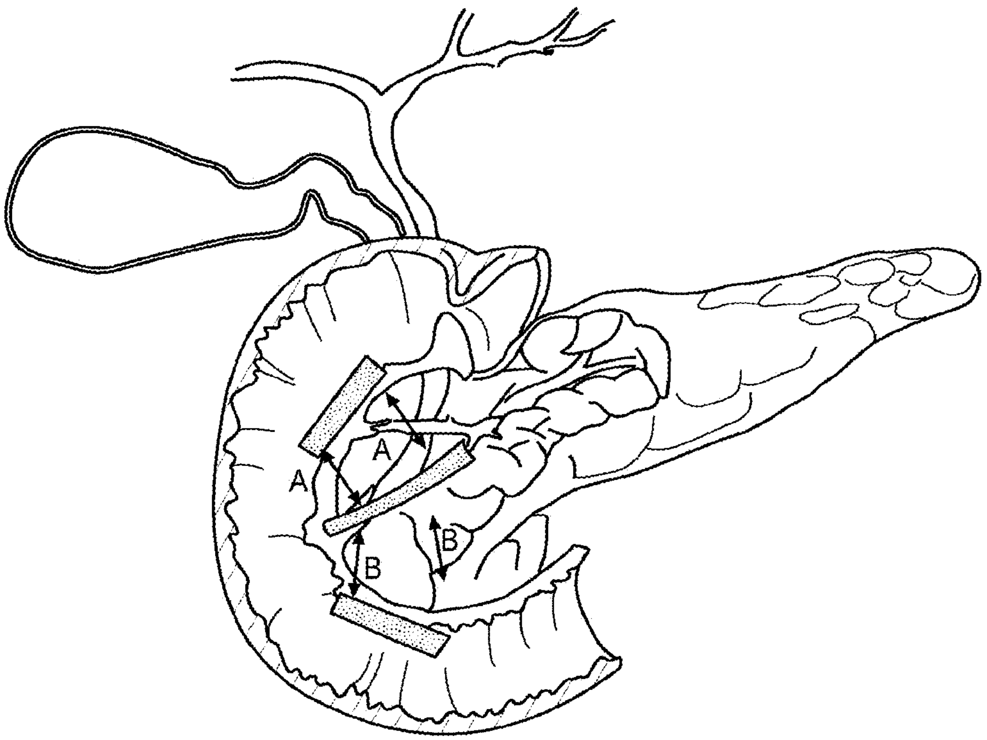
FIG. 16 shows a magnetic stent that can be delivered into the pancreatic duct. The stent can be coupled with a magnet in the stomach (A) or in the duodenum (B) to create a drainage anastomosis for the pancreatic duct.

The magnetic devices of the invention can also be used to treat pancreatic diseases. For example, the pancreatic duct requires decompression in certain disease states, such as chronic pancreatitis. Currently, extensive pancreatic duct decompression requires surgery (e.g., Peustow surgery in which the pancreas is filleted along the axis of the pancreatic duct and connected to a loop of small intestine for improved pancreatic drainage). As an alternative to Peustow surgery, extensive pancreatic duct decompression can be accomplished via creation of a large magnetic compression anastomosis between the pancreatic duct and either the stomach or duodenum using a magnetic pancreatic catheter, as shown in FIG. 16. The catheter can be magnetic along its entire length or only at certain intervals. The catheter can be in the form of a stent or straw. The pancreatic duct can be accessed using conventional ERCP methods (retrograde cannulation through the ampulla) or by direct needle access using endoscopic ultrasound (EUS). The magnetic pancreatic catheter can be delivered into the pancreatic duct and coupled with a second magnetic device in either the stomach or duodenum. As in the biliary scenario described above, the magnetic pancreatic catheter could be hinged to the second magnetic device.

Figure 17:
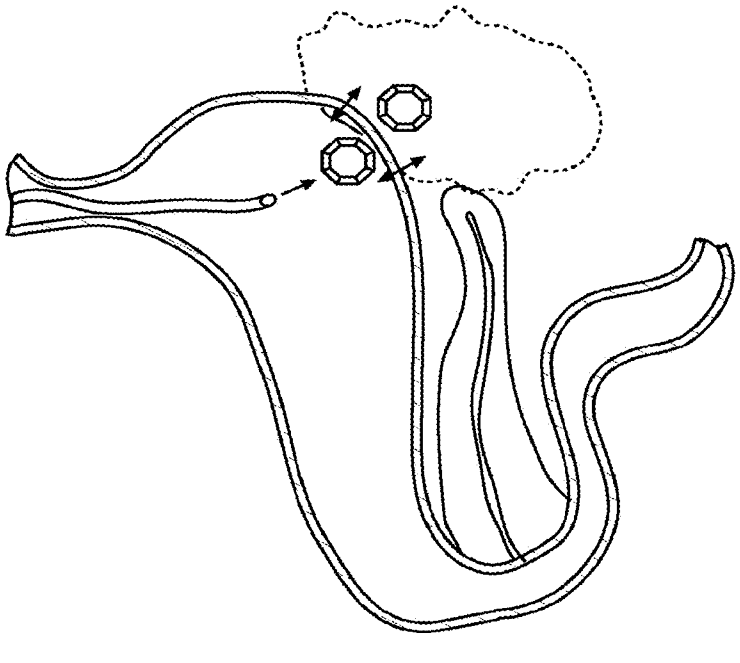
FIG. 17 shows a magnetic assembly that is delivered into a peripancreatic collection (dotted structure) using endoscopic ultrasound guided needle/catheter delivery which then couples with a second magnet assembly deployed in the stomach.

Self-assembling magnetic devices can also be used to access and drain fluid collections located adjacent to the gastrointestinal tract, as shown in FIG. 17. For example, following a bout of pancreatitis, pancreatic fluid collections can form that require drainage. While drainage can be accomplished using surgery or a percutaneous catheter, endoscopic drainage has been found to be more clinically and cost-effective, but can be complicated by bleeding, perforation, and/or inadequate drainage. As an alternative to surgical draining, magnetic devices of the invention can be delivered through a needle or sharpened catheter into the collection under endoscopic ultrasound (EUS) guidance, as shown in FIG. 17. Following assembly, the first magnetic device is coupled to the second magnetic device that has been placed in the gastrointestinal lumen (e.g. stomach). In order to speed removal after drainage, the first magnet may be tethered by a connecting wire as previously described. As described previously, the intervening tissue can be cut using electrocautery or dilation followed by needle and wire access. Additional devices, such as magnetic coupling clamps can be used to control blood flows to allow for "blood-less" endoscopic entry into the collection.

Figure 18:
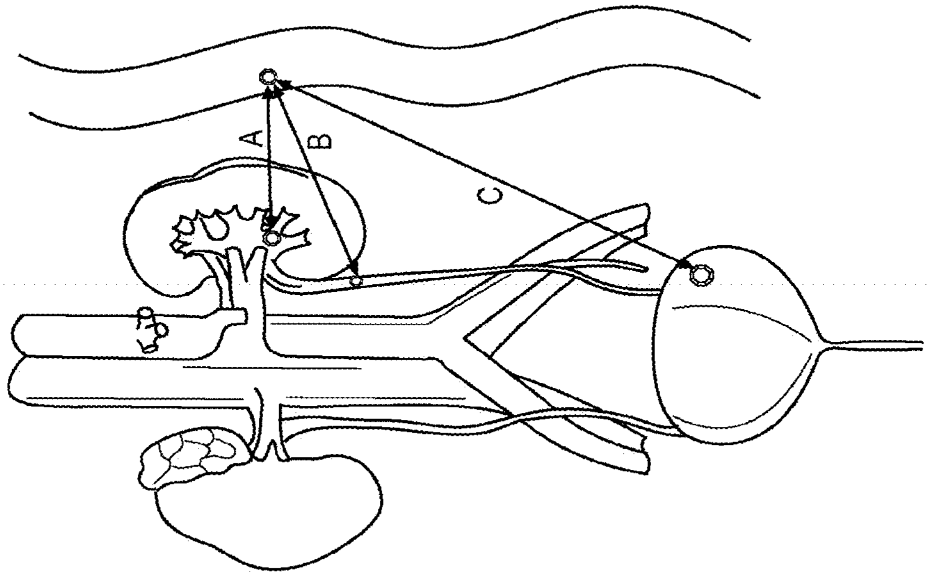
FIG. 18 shows different targets for anastomoses between the urinary system and the gastrointestinal system: renal calyx (A), ureter (B), and bladder (C).

Self-assembling magnets can also be used for urological applications such as forming bypasses to treat an obstructed urogenital tract, as shown in FIG. 18. For example, a magnetic anastomosis could be created between the renal calyx and bowel (A), between the ureter and bowel (B), or between the bladder and bowel (C). Self-assembling magnetic devices of the invention can be delivered into the urological tract using an endoscope, laparoscope, or needle, as described above. The reciprocal magnetic device could be delivered into the gastrointestinal tract using an endoscope, laparoscope, or needle as previously described. In other embodiments, the devices can be used for reproductive procedures, such as bypassing a portion of obstructed fallopian tube or bypassing a vasectomy.

Figure 19:
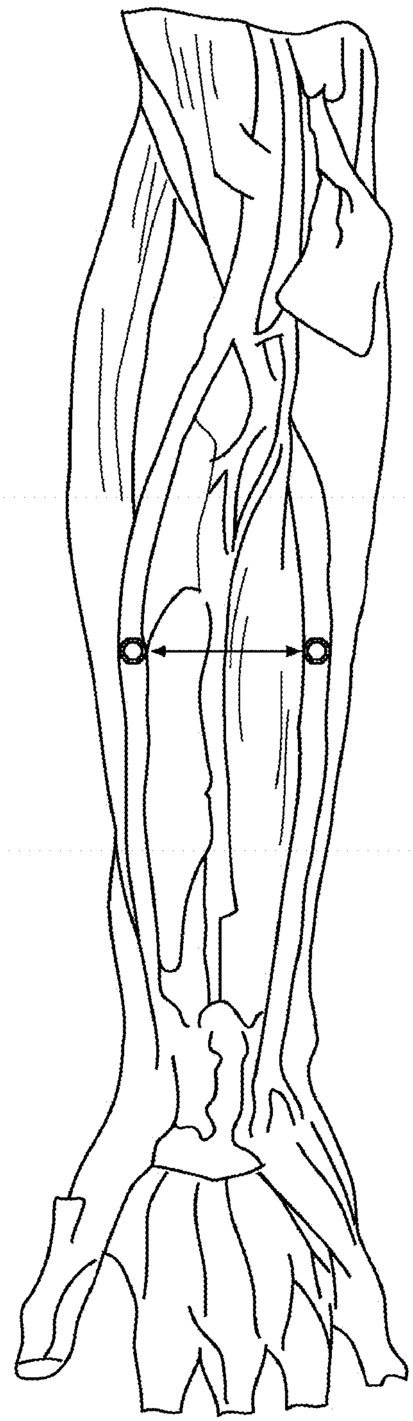
FIG. 19 shows magnet assemblies in adjacent blood vessels to couple and create a vascular anastomosis.

In yet another application, self-assembling magnetic devices can be used to create vascular anastomoses or to treat cardiac conditions. For example, a magnetic anastomosis coupling can be formed between adjacent blood vessels with magnetic devices, as shown in FIG. 19. In an embodiment, the self-assembling devices can be delivered with a vascular delivery device, such as a catheter. Additionally, as described above with respect to gallbladder and pancreatic applications, a shunt can be installed to bypass a portion of the vasculature that is weak or blocked.

Figure 20:
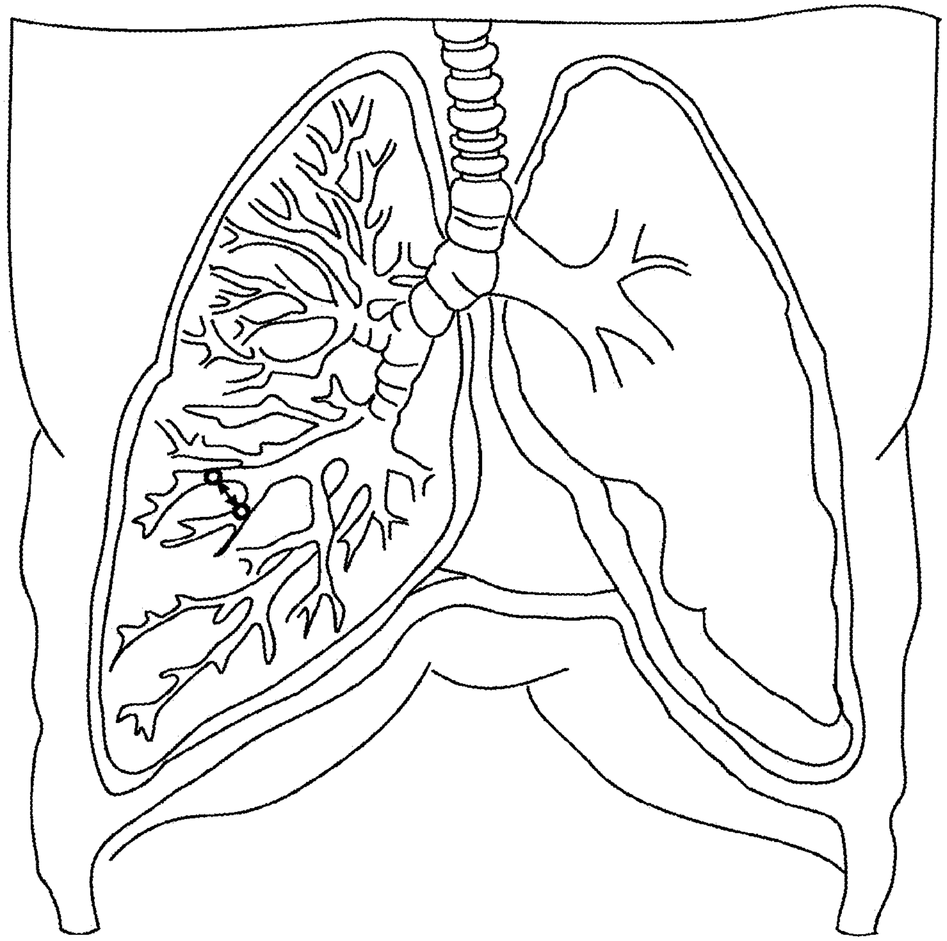
FIG. 20 shows magnet assemblies in different parts of the respiratory system to create anastomoses between adjacent bronchioles.

Self-assembling magnets can also be used for pulmonary applications such as forming bypasses in the airway to treat chronic obstructive pulmonary disease (COPD). For example, magnetic anastomoses can be created by deploying self-assembling magnetic devices into adjacent bronchioles, as shown in FIG. 20. Creation of pulmonary "bypasses" could lower airway resistance that characterizes respiratory diseases such as COPD.

Figure 21:
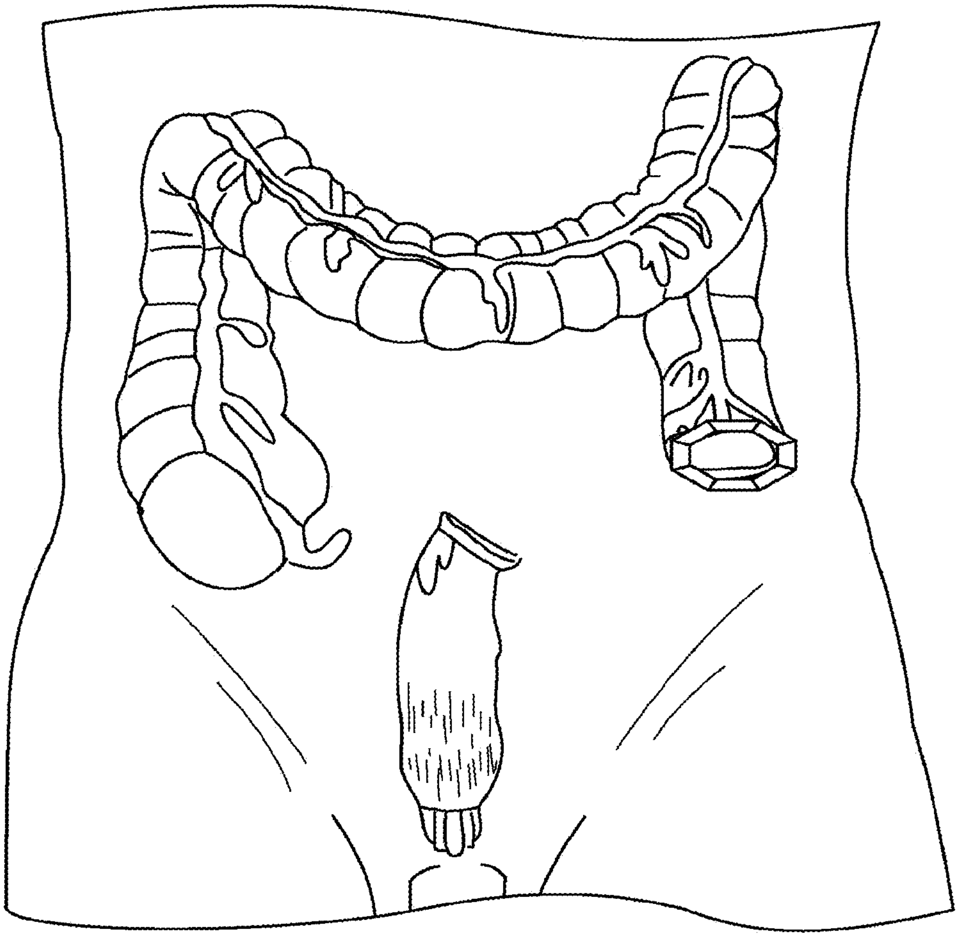
FIG. 21 shows an external magnet assembly and an internal magnet assembly within the gastrointestinal tract used to create a surgical stoma for fecal drainage.

Self-assembling magnetic devices can also be used to create surgical stomas for diversion of a fecal stream, e.g., into a colostomy bag. For example, a magnetic anastomosis can be created by deploying self-assembling magnets into the gastrointestinal tract (e.g. large intestine), as shown in FIG. 21, and then coupling the interior magnet to an external magnet worn and secured at the level of the skin. The exterior magnetic device may be coupled to yet a third magnetic device that is coupled to a collection device. Such a system allows easy removal of the collection device for cleaning, etc.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Various inventive concepts may be embodied as one or more methods, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein in the specification and in the claims, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Various embodiments of the present invention may be characterized by the potential claims listed in the paragraphs following this paragraph (and before the actual claims provided at the end of the application). These potential claims form a part of the written description of the application. Accordingly, subject matter of the following potential claims may be presented as actual claims in later proceedings involving this application or any application claiming priority based on this application. Inclusion of such potential claims should not be construed to mean that the actual claims do not cover the subject matter of the potential claims. Thus, a decision to not present these potential claims in later proceedings should not be construed as a donation of the subject matter to the public. Nor are these potential claims intended to limit various pursued claims.

Without limitation, potential subject matter that may be claimed (prefaced with the letter "P" so as to avoid confusion with the actual claims presented below) includes:

P1. A magnetic compression anastomosis device comprising a plurality of interconnected vertebrae including a first vertebra and a second vertebra, wherein each of the first vertebra and the second vertebra is a multipiece vertebra comprising a magnet at least partially encapsulated by a vertebra skin, and wherein the first vertebra and the second vertebra are interconnected by a cylindrical roller and at least one flex element, the roller and the at least one flex element at least partially encapsulated by the first vertebra skin and the second vertebra skin, the roller configured to allow the first and second vertebra to pivot through a predetermined range of rotation in a device plane between at least a delivery configuration and an assembled configuration while constraining movement in other degrees of freedom, the at least one flex element including oppositely-oriented first and second U-brackets that operate together with the roller and the first and second vertebra to bias the first and second vertebra toward the assembled configuration, wherein the first U-bracket is at least partially encapsulated by the first vertebra skin to secure the first U-bracket to the first vertebra, the second U-bracket is at least partially encapsulated by the second vertebra skin to secure the second U-bracket to the second vertebra skin, and the first and second U-brackets operate to hold the roller in place between the first and second vertebra.

P2. The device of claim P1, wherein the vertebra skin comprises at least one of a metal alloy, a polymer, or a composite material.

P3. The device of claim P1, wherein the vertebra skin comprises a shape memory material.

P4. The device of claim P1, wherein the vertebra skin is configured with at least one tissue cutting element.

P5. The device of claim P1, wherein the vertebra skin is configured with at least one tissue compression element.

P6. The device of claim P1, wherein the vertebra skin is configured with at least one tissue securing element.

P7. The device of claim P1, wherein each vertebra skin includes male nodes and female nodes at opposing ends of the vertebra skin.

P8. The device of claim P7, wherein the male nodes are configured to at least cover the ends of the roller and optionally to secure the roller in place.

P9. The device of claim P1, wherein the roller is a hollow cylinder.

P10. The device of claim P1, wherein the roller is a solid cylinder.

P11. The device of claim P9, wherein the first and second U-brackets fit through the roller.

P12. The device of claim P11, wherein the first and second U-brackets are secured by the roller.

P13. The device of claim P11, wherein the roller includes flex element supports to secure the U-brackets in a position that allows bias toward the assembled configuration.

P14. The device of claim P1, wherein U-brackets are formed of a shape-memory material.

P15. The device of claim P1, wherein the magnet of the first vertebra includes channels in which the first U-bracket is secured and the magnet of the second vertebra includes channels in which the second U-bracket is secured.

P16. The device of claim P1, wherein the vertebrae are aligned in a substantially linear arrangement in the delivery configuration.

P17. The device of claim P1, wherein the vertebrae are arranged in a circular arrangement in the assembled configuration.

P18. The device of claim P1, wherein the vertebrae are arranged in a polygon arrangement in the assembled configuration.

P19. The device of claim P1, wherein the vertebrae include a proximal end vertebra and a distal end vertebra that magnetically couple to one another in the assembled configuration.

P20. A magnetic compression anastomosis system comprising a delivery device comprising a lumen; and at least one magnetic compression anastomosis device according to claim 1 predisposed within the lumen of the delivery device in the delivery configuration.

P21. Individual magnetic vertebrae sections for a magnetic compression anastomosis device comprising: a vertebrae skin comprising a metal alloy, polymer, and/or composite material; a flex segment configured as a tensile member; a sprung flex member configured to aid in formation of an array; a roller configured to provide radial constraint and limit degrees of freedom to strengthen the array from a torsional standpoint.

P22. The vertebrae of claim P21 further comprising: a roller or node configured to create rotation in one plane while limiting torsional degrees of freedom in other planes; and stops configured to limit one or more degrees of freedom.

P23. The vertebrae of claim P21 further comprising: a male node of a first vertebra configured to interlock with a female node of a second vertebra wherein the vertebrae are shaped to provide interference allowing a prescribed amount of rotation around an axis of the male node and female node.

Although the above discussion discloses various exemplary embodiments of the invention, it should be apparent that those skilled in the art can make various modifications that will achieve some of the advantages of the invention without departing from the true scope of the invention. Any references to the "invention" are intended to refer to exemplary embodiments of the invention and should not be construed to refer to all embodiments of the invention unless the context otherwise requires. The described embodiments are to be considered in all respects only as illustrative and not restrictive.

What is claimed is:

1. A magnetic compression anastomosis device comprising:

a plurality of interconnected vertebrae including a first vertebra and a second vertebra, wherein each of the first vertebra and the second vertebra is a multipiece vertebra comprising a magnet at least partially encapsulated by a vertebra skin, and wherein the first vertebra and the second vertebra are interconnected by a cylindrical roller and at least one flex element, the roller and the at least one flex element at least partially encapsulated by the first vertebra skin and the second vertebra skin, the roller configured to allow the first and second vertebra to pivot through a predetermined range of rotation in a device plane between at least a delivery configuration and an assembled configuration while constraining movement in other degrees of freedom, the at least one flex element including oppositely-oriented first and second U-brackets that operate together with the roller and the first and second vertebra to bias the first and second vertebra toward the assembled configuration, wherein the first U-bracket is at least partially encapsulated by the first vertebra skin to secure the first U-bracket to the first vertebra, the second U-bracket is at least partially encapsulated by the second vertebra skin to secure the second U-bracket to the second vertebra skin, and the first and second U-brackets operate to hold the roller in place between the first and second vertebra.

2. The device of claim 1, wherein the vertebra skin comprises at least one of a metal alloy, a polymer, or a composite material.

3. The device of claim 1, wherein the vertebra skin comprises a shape memory material.

4. The device of claim 1, wherein the vertebra skin is configured with at least one tissue cutting element.

5. The device of claim 1, wherein the vertebra skin is configured with at least one tissue compression element.

6. The device of claim 1, wherein the vertebra skin is configured with at least one tissue securing element.

7. The device of claim 1, wherein each vertebra skin includes male nodes and female nodes at opposing ends of the vertebra skin.

8. The device of claim 7, wherein the male nodes are configured to at least cover the ends of the roller and optionally to secure the roller in place.

9. The device of claim 1, wherein the roller is a hollow cylinder.

10. The device of claim 2, wherein the first and second U-brackets fit through the roller.

11. The device of claim 10, wherein the first and second U-brackets are secured by the roller.

12. The device of claim 11, wherein the roller includes flex element supports to secure the U-brackets in a position that allows bias toward the assembled configuration.

13. The device of claim 1, wherein the roller is a solid cylinder.

14. The device of claim 1, wherein the U-brackets are formed of a shape-memory material.

15. The device of claim 1, wherein the magnet of the first vertebra includes channels on opposite sides of the magnet in which the first U-bracket is secured and the magnet of the second vertebra includes channels on opposite sides of the magnet in which the second U-bracket is secured.

16. The device of claim 1, wherein the vertebrae are aligned in a substantially linear arrangement in the delivery configuration.

17. The device of claim 1, wherein the vertebrae are arranged in a circular arrangement in the assembled configuration.

18. The device of claim 1, wherein the vertebrae are arranged in a polygon arrangement in the assembled configuration.

19. The device of claim 1, wherein the vertebrae include a proximal end vertebra and a distal end vertebra that magnetically couple to one another in the assembled configuration.

20. A magnetic compression anastomosis system comprising:

a delivery device comprising a lumen; and at least one magnetic compression anastomosis device according to claim 1 predisposed within the lumen of the delivery device in the delivery configuration.

* * * * *